(12) United States Patent
Oon

(10) Patent No.: US 7,321,861 B1
(45) Date of Patent: Jan. 22, 2008

(54) AUTOMATION ORIENTED HEALTHCARE DELIVERY SYSTEM AND METHOD BASED ON MEDICAL SCRIPTING LANGUAGE

(75) Inventor: Yeong Kuang Oon, 29 Darryl Street, Scoresby, Victoria (AU) 3179

(73) Assignee: Yeong Kuang Oon, Scoresby, Victoria (AU)

( * ) Notice: Subject to any disclaimer, the term of this patent is extended or adjusted under 35 U.S.C. 154(b) by 0 days.

(21) Appl. No.: 09/786,566

(22) PCT Filed: Sep. 8, 1999

(86) PCT No.: PCT/AU99/00736

§ 371 (c)(1), (2), (4) Date: Mar. 7, 2001

(87) PCT Pub. No.: WO00/14652

PCT Pub. Date: Mar. 16, 2000

(30) Foreign Application Priority Data

Sep. 9, 1998  (AU) .................................... PP5772

(51) Int. Cl.
  *A61B 5/00*  (2006.01)
  *G06F 19/00*  (2006.01)
(52) U.S. Cl. .............................................. 705/3; 704/9
(58) Field of Classification Search .................... 705/3; 704/9
  See application file for complete search history.

(56) References Cited

U.S. PATENT DOCUMENTS 5,404,528 A * 4/1995 Mahajan ..................... 719/320
5,475,805 A * 12/1995 Murata ........................ 715/513
5,594,638 A * 1/1997 Iliff ................................ 705/3
5,772,585 A   6/1998 Lavin et al. ................ 600/300
6,055,494 A * 4/2000 Friedman ........................ 704/9
6,182,029 B1 * 1/2001 Friedman ........................ 704/9
6,684,188 B1 * 1/2004 Mitchell et al. ............... 705/3
6,810,522 B2 * 10/2004 Cook et al. ................ 719/316
2003/0073887 A1 * 4/2003 Iliff ............................. 600/300
2004/0249667 A1 * 12/2004 Oon ............................... 705/2

FOREIGN PATENT DOCUMENTS

| WO | WO 96/41275 | * 12/1996 |
| WO | WO 97/32271 |   9/1997 |
| WO | WO 97/48059 | * 12/1997 |

* cited by examiner

*Primary Examiner*—Jeffrey A. Smith
*Assistant Examiner*—Russell Shay Glass
(74) *Attorney, Agent, or Firm*—Leydig, Voit & Mayer, Ltd.

(57) ABSTRACT

A medical record management system administrator comprising: (a) a data receiver to selectively receive one or more medical files pertaining to a first patient, each file represented in a medical scripting language having predetermined syntactical and semantic constructs; (b) a recorder to record and store each medical file of the patient in terms of the predetermined syntactical and semantic constructs; and (c) a query module to receive a query from a predefined source which has been assigned selective access to the recorded material in terms of the predetermined syntactical and semantic constructs, and to transmit relevant recorded material to that source.

10 Claims, 4 Drawing Sheets

Figure 1:
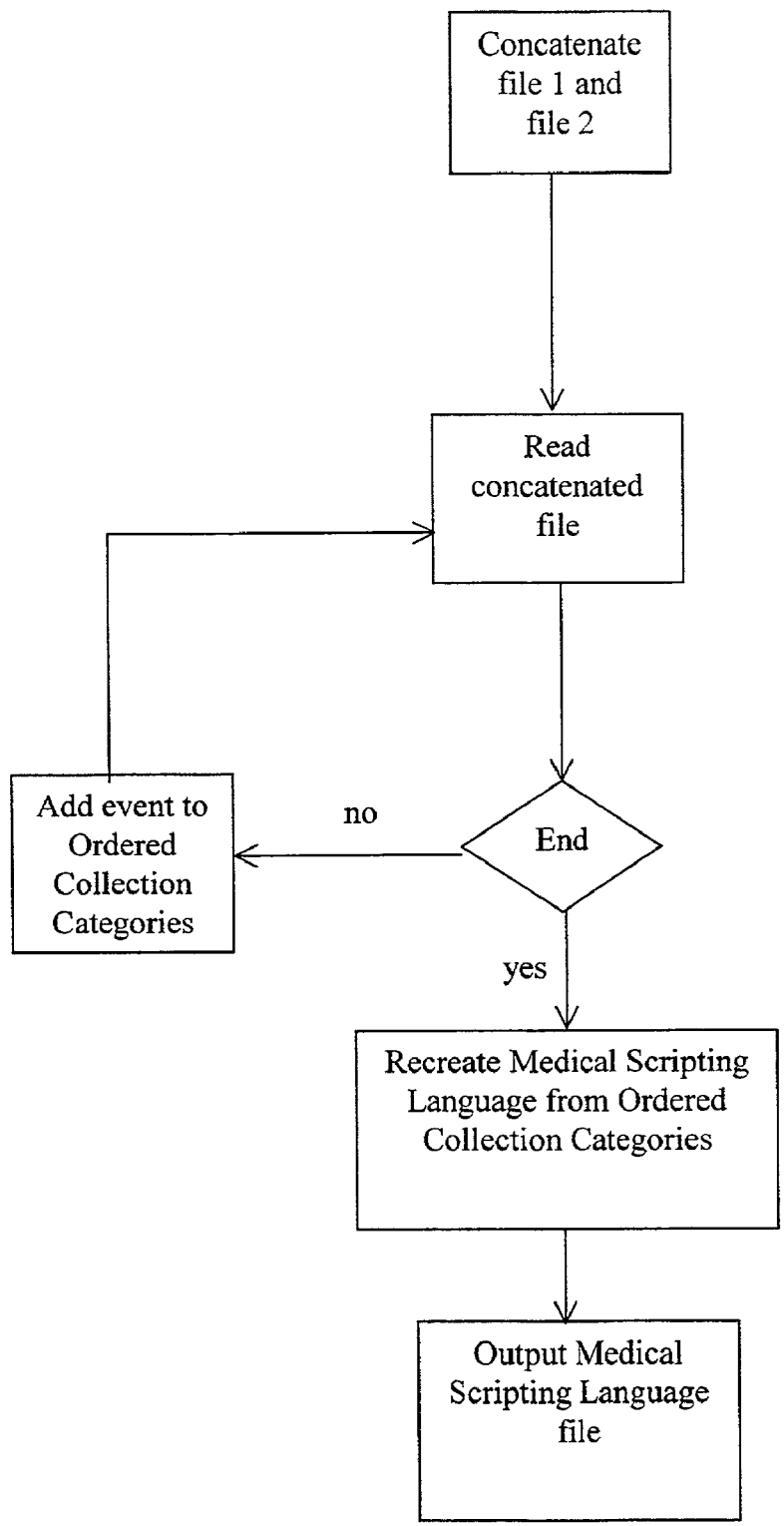

The ADD operation on two Medical Scripting Language files

Graphical print out of graphic element embedded in Table 3 medical scripting language file.

AUTOMATION ORIENTED HEALTHCARE DELIVERY SYSTEM AND METHOD BASED ON MEDICAL SCRIPTING LANGUAGE

FIELD OF THE INVENTION

This invention relates to a system administrator, a management system and a method for automation oriented healthcare delivery using a medical scripting language having predetermined syntactical and semantic constructs.

BACKGROUND OF THE INVENTION

Good health is the concern of any global citizen. Computerization has the potential to help automate many aspects of healthcare. Among them being automated recalls and reminders, decision support with "what-if" clinical problem solving and collaborative singular patient problem solving by a plurality of healthcare workers sharing a standard patient file that is functional across any computer operating system platform and computer network. Automation of healthcare is impaired by the lack of a viable universal transportable medical record that can fully encapsulate the total patient experience of all medical events and ongoing treatment and management of a patient. Patient's needs include prescriptive recalls for periodic health checks or management tasks based on specific disease diagnostic and management protocols.

In the internet era, where knowledge is supposed to flow freely, modern medicine is incongruent in the sense that medical knowledge is packaged in a manner that is incomprehensible to most. The medical decision making based on scientific facts available to the practitioners is often a process that totally excludes the input of the intelligent patient. This old paradigm, in the machine age, when patient has access to very comprehensive information on the world wide web, is possibly in need of transformation. Modern medicine has often exalted the elitism of the medical profession and has in the main rejected or downgraded the possibility of the patient helping to diagnose and solve his own problems. This has led to occasional patient frustration spilling over to litigation. The medical profession may have reacted and practice in a manner that is adapted to avoid litigation rather than providing best care. The cost of medical care is escalating in modern society for a number of reasons. Modern medicine has seen the proliferation of sophisticated laboratory and imaging test with its attendant costs. With the plurality of service providers, it is economic from the healthcare budget angle and in the patient's interest to not only avoid duplication of tests, but to do these tests intelligently with the help of software.

Increasingly the goal of medicine is evidence based medicine/best practice where the management is strictly set out in protocols with time components. An example of such a protocol is that regarding the management of diabetes mellitus. Nowadays the current best practice for management of diabetes mellitus requires:
1) initial referral to dietician and or diabetic educator;
2) twice a year glycated hemoglobin (HbA1c) tests;
3) annual review by opthamologist;
4) yearly checks for microalbuminuria;
5) yearly check by podiatrist; and
6) frequent home glucometer checking.

With increased societal affluence and educational level, citizens expect the best and optimal care. These factors conspire to drive up health costs.

Aggravating the situation are:
1) the existence of inefficiencies such as repeating unnecessary laboratory and imaging tests due to poor record keeping;
2) drug to drug interactions;
3) disease drug interactions;
4) poor analysis of symptoms and signs from the viewpoint of insufficient physician time;
5) restrictive work practice of the healthcare industry where the patient is locked out by an elitist medical profession: this often leads to a poorly informed patient;
6) poor decision making that is tainted/driven by litigation avoidance;
7) the lack of a collaborative framework whereby all healthcare workers and the patient can pool their resources together to help fix the patient's problems; and
8) the recent phenomenon of patient queries arising from medical knowledge gleaned from dredging the internet. This is a natural desire by intelligent and often internet savvy patients to "manage" their own medical conditions.

The doctor suffers the deluge of data generated by the practice of modern medicine; with the proliferation of tests and the need for tracking the results of these tests, drug adverse reactions and interactions. There has been a veritable data explosion in the field of medicine associated with real advances in medicine. But how do we convert all this data to knowledge and wisdom to impact favourably on the health of our patient?

In summary, the patient and the healthcare profession face the following problems:
1) Patient's poor understanding of his own overall health problems and lack of knowledge tools to dissect his medical conditions.
2) Patient's poor understanding and lack of access to reliable recordal means of the sequence of events such as laboratory and radiological tests relating to his health problems and inability to access his own record on the internet or computer network. In an ideal situation, the patient has the means to log on to his internet browser to find out his latest lipids results.
3) The patient is effectively disenfranchised from decision making, based on scientific facts relating to his health problems due to the lack of an "independent machine expert" working on his medical status based on his medical record. Hitherto, there is no effective electronic transportable medical record framework for decision making.
4) Attendant risks due to poor medical record keeping arising from the fragmented nature of medical care by multiple carers over time and geographical spread resulting in fractured medical records.
5) The lack of a write once, run anywhere computer medical record with built-in embedded health protocol commands, regardless of computer platform. The absence of an effective transportable electronic medical record capable of fully representing patient status and ongoing management tasks based on standards such as a text file of ASCII or even Latin-1 subset or UNICODE characters.
6) With the prior art, the medical records that are passive with data held in database fields, these data are aggregated/searched/processed and viewed by a process of SQL queries. This passive structure of current electronic medical record design is contrasted with the need for patient records to include active executive commands. This set of commands would need to be individually tailored to each patient.

7) With the prior art, the record keeping computer program analyses every record to see if a record qualifies for action to undertake preventive action/initiate medical action—for example, an adult woman is to seek a periodic pap smear and a periodic mammogram; a man over the age of 40 is to get his blood pressure checked every year. In the invention detailed here, the patient file has embedded commands individually tailored for each patient. Each individual command will each launch its own protocol.

8) Poor co-ordination among a multitude of health providers. In an ideal situation, a health provider such as the family physician or specialist should be able to get an accurate run down on a list of active problems, a list of medications, lists of imaging and non-imaging test results and other related health information; this is to avoid the repetition of a test in ignorance of the fact that it was recently done. The ideal medical record must be able to provide "in a nutshell ability".

9) Current implementation of electronic medical records held in a network is plagued by privacy constraints. In this invention, the concept of headerless anonymous patient files written in medical scripting language is proposed as a way to obviate the problem.

10) Healthcare costs is aggravated by the time consuming nature of history taking and decision making. Significant cost savings can be derived if the patient can present a list of properly defined and analysed symptoms during consultation with the doctor and a comprehensive medical history and management work sheet arrived at by the patient himself using the client spreadsheet browser. His file written in medical scripting language and interacting with the supervisory program detailed in this invention.

11) With present electronic medical record systems, the consumer is locked out of the chance to view and have a say about his medical data, and is a passive element in the healthcare process.

12) A lack of access to a congruent set of patient data anywhere and anytime. The pervasive internet fulfils the criteria of being online everywhere and every time as long as the network is up. The invention detailed below leverages on this fact and allows decisiveness at the moment of choice in healthcare.

The ideal healthcare system must empower the patient. In this internet age, the advance of educational level, the interest in health matters by consumers—there is potential for a win-win partnership between the patient and the collection of stakeholders in the business of healthcare. This invention discusses the framework and implemented steps to bring this about.

SUMMARY OF INVENTION

This invention in a first embodiment relates to a medical record management system administrator comprising:
(a) a data receiver to selectively receive one or more medical files pertaining to a first patient, each file represented in a medical scripting language having predetermined syntactical and semantic constructs;
(b) a recorder to record and store each medical file of the patient in terms of the predetermined syntactical and semantic constructs; and
(c) a query module to receive a query from a predefined source which has been assigned selective access to the recorded material in terms of the predetermined syntactical and semantic constructs, and to transmit relevant recorded material to that source.

In a second embodiment of the invention, a computerised medical record management system is provided comprising:
(A) an administrator comprising:
  (a) a data receiver to selectively receive one or more medical files pertaining to a first patient, each file represented in a medical scripting language having predetermined syntactical and semantic constructs;
  (b) a recorder to record and store each medical file of the patient in terms of the predetermined syntactical and semantic constructs; and
  (c) a query module to receive a query from a predefined source which has been assigned selective access to the recorded material in terms of the predetermined syntactical and semantic constructs, and to transmit relevant recorded material to that source;
(B) a browser to issue search query commands to the query module and to receive and transmit the outcome of the query module to a predetermined source; and
(C) a data input/output screen to input one or more medical files pertaining to the first patient to the data receiver and to receive from the browser, the transmitted outcome of the query module.

In a third embodiment of the invention, there is provided a method for medical record management system administration comprising:
(a) selectively receiving one or more medical files pertaining to a first patient, each file represented in a medical scripting language having predetermined syntactical and semantic constructs;
(b) recording and storing each medical file of the patient in terms of the predetermined syntactical and semantic constructs; and
(c) processing at least one a query from a predefined source which has been assigned selective access to the recorded material and transmitting the relevant recorded material to that source.

The invention is adapted to be installed on a standalone machine or alternatively, on a local area network/wide area network/intranet/internet.

The inventions are based on a transportable human readable/machine parseable patient medical files/records coded in a medical scripting language which preferably also has embedded executive commands for enabling pre-emptive healthcare actions to be carried out, with shape change tolerant keywords, and comprising means for patient medical problem solving utilising knowledge spreadsheeting.

The administrator is typically located on a server or merely at the client level. This administrator program comprising means to interpret and execute the medical scripting language as a computer program of stored instructions and data.

This administrator may perform in association with suitable patient file browsers ranging from standard Mosaic derived Internet browsers to a knowledge based medical spreadsheet to extend the spectrum of medical input and decision support in patient management to include all health workers and optionally the patient himself or herself, by the reading and manipulation of the patient medical file represented in the described medical scripting language.

DETAILED DESCRIPTION OF THE INVENTION

Medical Scripting Language

One integral feature of the invention is the use of a medical script language which has been characterised as having predetermined syntactical and semantic constructions. The following description is an illustration of what this comprehends. It is not intended to be exhaustive of all manifestations of this language, the essential requirements of which are merely the features of syntactical and semantic constructions.

The unique structure of Medical Scripting Language (MSL) is its commutative/associative features, especially of addition (and less so subtraction) operations on separate/disparate MSL files of a single patient. The two most distinctive features are 1) commutative/associative add/subtract features 2) embedded commands in a patient file to make it "ACTIVE" and capable of healthcare actions—this is user programmable and uniquely tailored to each patient.

Patient care often occurs in multiple locations over a series of encounters with various health practitioners and investigative laboratories. There is a constant need to merge the various streams of data, examples are pathology/radiology reports, specialist findings and hospital discharge summaries.

Medical scripting language breaks down clinical and non-clinical data into events. For instance, the sex of the patient is an administrative event. On enrolment in the clinic in June 1992, the event recording his sex shows that he is male. Six years later the patient has a sex change:

1 Jun 1992 sex%m
23 Aug 1998 sex%f

Likewise for street addresses and phone numbers each change will be associated with a data stamp.

Because of the strict definition of the medical scripting language as a high level language with strict syntax and semantic rules, patient data that is represented as MSL in a pathology report, a specialist clinical record system or general practitioner system, are all commutative and can be merged or subtracted with impunity and total integrity. There is no need to resolve any administrative data conflict, such as street addresses, as any variations in administrative/clinical data are simply incorporated as events which are data and time stamped.

It is the commutative/associative nature of the design of MSL for both addition and subtraction operations that overcomes the conundrum of health/administrative data held in disparate locations over time.

The Addition Operation

For example if Record A represents a general practitioner medical record and Record B represents a pathology report on a single blood test on the same patient:
Record A+Record B=Record C. Likewise Record B+Record A=Record C.

In mathematics and logic, any operation that involves two objects and gives the same result, independent of order, is said to be commutative.

In that sense Medical Scripting Language is commutative for addition or merger of two records.

Representing all medical data pertaining to the same patient in multiple locations allows for the just-in-time virtual medical record where the MSL from multiple locations are pooled into a single workstation:
(Record A+Record B+Record C)+(Record D+Record E+Record F)=Record G
(Record A+Record B)+(Record C+Record D+Record E+Record F)=Record G In mathematics and logic, any operation that involves objects and gives the same result independent of grouping is said to be associative.

In that sense Medical Scripting Language is associative for addition or merger of more than two records of the same patient.

In summary, MSL is both associative and commutative for the addition or merger of patient records.

The Subtraction Operation

Record A represents a general practitioner medical record and Record B represents a pathology report on a single blood test:
Record A+Record B=Record C.
Likewise: Record C−Record B=Record A.
Likewise: −Record B+Record C=Record A.

In mathematics and logic, any operation that involves two objects and gives the same result independent of order is said to be commutative.

In that sense Medical Scripting Language is commutative for subtraction and allows for reversion to its original state by reversing the previous add operation.

Representing all medical data pertaining to the same patient in multiple locations allows for the just in time virtual medical record where the MSL from multiple locations are pooled into a single workstation:
(Record A+Record B−Record C)+(Record D+Record E+Record F)=Record G
(Record A+Record B)+(−Record D−Record C+Record E+Record F)=Record G In mathematics and logic, any operation that involves objects and gives the same result independent of grouping is said to be associative.

In that sense Medical Scripting Language is associative for subtraction of records. Subtraction of records is of relevance in suppression of sensitive medical data, when data is disseminated on a need to know basis only.

This system of updating medical files by operating on disparate MSL files belonging to a single patient delivers improved integrity attributed to the share structure of each medical scripting language file with its embedded administrative data. A cross check of administrative data in each respective medical scripting language file will ensure that patient A data will not be inadvertently put into patient B file.

Providing that all healthcare providers utilise the MSL format, this will lead to simplification of doing the electronic updating of medical records and achieve the universal transportable medical record functionality.

In summary MSL is both associative and commutative for addition and subtraction of medical records for the benefits of simplicity of operation and data integrity. In the preferred environment of all health care providers using MSL, there need be only one standard interface of updating the patient medical file.

Considering the MSL in more detail, for ease of communication, the appellations of "DocleScript" of "MSL" are sometimes used hereafter interchangeably to describe this medical scripting language. The terms "patient file" and "patient record" are also used interchangeably herein.

A patient file may be stored as a computer text file or held as a very long string of characters in a single field or multiple fields in a computer record of a database system. Alternatively, a logical equivalent of a patient file is a persistent programming object.

A patient file written in medical scripting language integrates patient care by its means to represent every tiny medical event that has happened to the patient. This file, written in medical scripting language, is human readable. This implies the power of expressivity describing medical conditions that can approach the flexibility of natural language processing. Because medical scripting language is constructed like a high level computer language, the patient medical file in this invention can be interpreted or compiled by a computer program.

The structure of medical scripting language is defined in Extended Backus Naur Format, this same EBNF format is used to express high level computer languages such as Modula (Programming in Modula-2 by Niklaus Wirth, spronger Verlag 1982) and Smalltalk (Smalltalk V, Digitalk corporation 1992). Medical scripting language as an advancement on the manual and electronic medical record is analogous to what Java is to programming language on the internet. DocleScript and Java are like any high level computer languages; there are syntax rules and predefined keywords. The key difference between medical scripting language and, say Java, is that in Java there are approximately 48 keywords, whereas medical scripting language has in excess of sixteen thousand keywords, with more to be defined. Whereas an error in a keyword in a programming language such as Java will cause a program to halt, the MSL keywords can be deprecated with no loss of function through its shape change tolerant nature.

Each keyword in medical scripting language is a Docle expression. Docle is an alphabetic notational, coding and linnean classification system used in clinical medicine invented by this author. Medical scripting language is the glue that holds together the disparate three components of the framework comprising the medical scripting language itself, the supervisory program and the patient browser/spreadsheet.

The preferred future embodiment of this patient file is a computer file of the Unicode character set. The preferred current embodiment of this invention is with a subset of Unicode known as the ASCII (American Standard Code Information Interchange) character set, for the reason of compatibility with current keyboard design.

A patient data file becomes a universally transportable medical record when it is coded in a computer parseable, human readable medical scripting language and held as a string, based on the ASCII character set, such as in this embodiment and future embodiments that may include the complete unicode character set. This patient file structure may be a computer field, a computer record, or a computer file or a programming object. This patient file represents patient status and includes means for embedded executive commands for invoking the administrator program to run the designated protocols to effect healthcare actions.

Medical scripting language possesses many aspects of a computer program with its task oriented stored instructions and strong syntactical structure with computer keyword constructs. Yet it is a self modifying program. For example, after it executes a command of patient notification, it changes itself to record this fact so that the command is not repeated for a period. Yet medical scripting language also plays the role as a passive data file.

Representing a patient medical file in medical scripting language and placing this file on a secured network such as a virtual private internet (or using the alternative option of a headerless patient file in public networks such as the internet), opens all the health data pertaining to any individual patient for access to the multiplicity of health workers and optionally the patient himself.

Representing the patient data in medical scripting language also opens up the possibility of collaborative problem solving by a team of healthcare workers that may include the patient himself.

Medical scripting language allows the inclusion of commands (with programming arguments) that will launch protocols that will effect health actions such as a reminder by email.

Medical scripting language structures the patient file into sections that view the medical record as a collection of time stamped 1) administrative 2) commands 3) actions 4) presentation—not yet defined data 5) links—about to be defined data 6) unity—well defined data and 7) management data. This scheme is a prerequisite and is foundational for use of the patient medical file with a patient browser termed a medical spreadsheet or knowledge spreadsheet where the data has to be allocated to a plurality of cells. This is described in more detail later in this specification.

Medical scripting language allows the comprehensive coding and mapping of all medical entities held in the patient file and allows the decision support processing needed. Typically, in the patient medical scripting language file, the events are further tagged as negative, neutral, active or inactive. A summary abstract of this patient's medical data comprising all global active medical events and global inactive events is a powerful enabling tool for the physician at any point in the global to quickly evaluate a patient's general medical condition. Medical scripting language has a HTML (hypertext markup language) equivalent and it is possible to do a round trip conversion of MSL to MSL-HTML and back to MSL again. This capability extends to future flavours of SGML such as XML.

The Administrator

Another integral feature of the invention is the administrator. The following description is an illustration of what this comprehends. It is not intended to be exhaustive of all manifestations of the administrator. Other practical embodiments of the administrator can be found under the heading of More detailed Description of the Administrator appearing later.

The administrator has a built-in transcendent medical belief system. Transcendant in the sense that, if one takes the Docle coding and classification system explained above, codes are assigned for all medical objects and objects of all medical thought. The administrator or supervisory program can be located at the server or in special cases at the client level. This supervisory program comprises means to interpret and execute the patient file written in medical scripting language. Protocols or tasks are invoked by embedded commands held in the patient file.

All patients are different; they require individually tailored protocols relating to their conditions. Only a diabetic patient requires a protocol to prompt for six monthly glycated hemoglobin tests. It is the role of the supervisory program to launch each protocol as nominated by the commands listed in the patient file. It is the role of the supervisory program to launch a drug-drug or disease drug interaction protocol each time the patient file is updated.

The supervisory program has built-in protocols to act in the event of oversight to detect these drug-drug interactions and disease-drug interactions. The supervisory program has a built-in medical belief system and can respond to enquiries from client browsers using a knowledge spreadsheet tool to effect what-if analyses. The supervisory program can respond to an internet client request with a patient file coded in MSL-HTML format to be downloaded, to enable reading of the patient file using a standard internet Mosaic browser such as Netscape or Internet Explorer. Alternatively, the server can download the MSL as is, to be viewed within a text box in the internet browser. Alternatively, the MSL-HTML document can be configured to include tables, picklists, buttons and controls to enable the web client to have a spreadsheet application on his web browser.

Other embodiments of this framework has the web client running this medical spreadsheet application using Distributed Smalltalk, plug-ins for Web Browser such as a Smalltalk plug-in, Java, JavaScript, Java Beans, Active-X, VB Script or any newer method of implementing client Server Web applications, but all using the patient files written in medical scripting language format.

Browser

Another integral feature of the combined computerised medical management system is the browser use. The following description is an illustration of what this comprehends. It is not intended to be exhaustive of all manifestations of the browser.

A variety of browsers ranging from stock internet browsers to specialised medical knowledge spreadsheets to view the MSL patient file are available. The healthcare personnel and the patient can interact with the MSL patient file which represents the total database of the Patient's longitudinal health record.

Any standard internet Mosaic browser such as Netscape or Internet Explorer will be able to view the patient file as the supervisory program comprises means to repackage the patient DocleScript ASCII text file into HTML format. The patient browser has a utility to convert a DocleScript patient file into HTML, XML and SGML format termed DocleScript-html. Alternatively DocleScript-html can be converted to plain DocleScript with all the HTML tags stripped off. Either way such a patient file can be viewed with a text editor such as Microsoft Notepad.

One specialised browser for this internet health system is a knowledge spreadsheet tool called a medical spreadsheet, which is the subject of international patent application no. PCT/AU97/00362 filed under the heading "Iterative problem solving technique" This medical spreadsheet tool operates on the patient file encoded in medical scripting language. This spreadsheet tool is the preferred way for updating and interacting with the MSL patient file.

Internet Application

In the preferred embodiment of this invention, the system is internet based. The patient files are held in an internet server as the administrator with an adequate firewall to ward off unwelcome intrusions.

In one embodiment, the privacy of patient data is enhanced by using a headerless medical scripting language file. This file has all its administration data suppressed except for a lock string. This lock string "docks" with the password key of the retrieval request. The security wall will arbitrate the request with the patient key—password key combination provided. If the password key matches the lock, the file is returned. This type of security is ideal in the situation where the doctor is the custodian of the patient MSL file. The administrative data component is held in the family doctor's office. Any information leak at the server/internet server provider level is less serious.

The administrator supervisory program makes a daily mark and sweep of all the patient files such that every single patient file is interpreted and any embedded commands executed. The result of such an execution of a command may result in an email reminder being sent to the patient. This action is logged by modification of the patient file itself, and notification is also sent to the primary care physician and medical specialists.

Benefits of Various Embodiments of the Invention

Addressing the specific problems enumerated in the background section.

This system and method for machine augmentation of healthcare will enhance and empower the patient with ready access to his medical record, such as the tracking of test results, and the ability to manipulate personal health data with a knowledge spreadsheet.

The invention comprises a transportable electronic patient record in MSL, with a framework suitable for problem solving using a knowledge spreadsheet and automatic triggering of health actions by a supervisory program. The network oriented nature of the system comprises means for access across the globe.

The patient file is a string of characters based on the ASCII/unicode standard, hence it is compatible with any computing platform. The patient file in medical scripting language is an active entity as it contains individually tailored prescriptive commands to invoke protocols in the supervisory program. The patient file held in a central server is the answer to duplication of patient data held in disparate files. The administrative headerless patient files concept is one way to ameliorate the problem of privacy.

The time consuming nature of medical analysis of symptoms/signs and clinical thinking can have its cycle shortened by the patient doing his homework on the medical spreadsheet and presenting to his clinician a more clearly defined reason for consultation—saving immense time. With optional patient access to his electronic file, the integrity of his medical file is enhanced as the patient verifies the data. The pervasiveness of his medical file in the intranet/internet embodiment allows integrity of decision making in the event that the patient is seen in multiple locations.

More Detailed Description of the Administrator/Management System

In one particular manifestation of the administrator, the supervisory program comprises three components
1) the Medical Scripting Language Interpreter,
2) the Protocol Invocation Method, and
3) the PLUM medical belief system and query language system 1. The Medical Scripting Language Interpreter The interpreter builds up a virtual image of the patient by the use of dynamic data structures called OrderedCollections. These OrderedCollections are named according to the categories of medical data of a) Administrative b) Commands c) Actions d) Presentation e) Links f) Unity g) Management. The virtual image of the patient is constructed by populating these OrderedCollections with events held in the patient file coded in medical scripting language.

Before the interpreter can execute the embedded commands held in the patient file, the patient virtual image needs to be built up first.

The interpreter constructs the virtual patient image represented in the patient file by iterating through the following cycles.

The state of the interpreter
1) CurrentPatientName is a variable that holds the unique identifier to the patient file.
2) EventMode is a variable that sets the indicator to direct where each event is to be placed in one of the OrderedCollections of events.
3) The named OrderedCollections of:
   a) #administrative
   b) #commands
   c) #actions
   d) #presentation
   e) #links
   f) #unity
   g) #management
   h) #book
   i) #images@polyline
   j) #images@bmp The interpreter will then proceed with the following steps:
1. locate the patient file.
2. open file or record.
3. while not at end, rad next line comprising string of characters up to "l" token.
4. if at end of file, then close file and exit interpreter for now.
5. evaluate if change in the event mode, if so, change event mode and go back to 3.
6. add event to OrderedCollection set by event mode.

Having built up the virtual patient image, the interpreter now invokes the protocols as requested in the Commands OrderedCollection.

2. The Protocol Invocation Method (Allowing for Pre-emptive Actions)

If the system can print monthly prescriptions for the patient without the doctor's intervention, this would be a type of pre-emptive task.

The term pre-emptive in this context means 'to act for oneself before others'. Medical scripting language supports pre-emptive tasking.

The protocol method is implemented to signal to the patient or health worker the need to take a decisive health action such as having
(a) their blood pressure checked,
(b) a pap smear, or
(c) a cholesterol test etc.

The protocol parameters are:
1) date the command activity was inserted,
2) repeat recall factor, which is the interval between two similar actionRequests of preventive activity inserted,
3) date of last action fulfilling activity specified in protocol,
4) date of last actionRequest for activity.

In the Smalltalk embodiment of the program, all the protocols held inside the patient file are executed by the following program instruction:

Commands do: [:x|self protocol:x]

Where
  Commands is the OrderedCollection of command events.
  x is a local variable that instantiates to the value of each event as the do loop iterates through each element of the Command OrderedCollection.

The protocol:commandString method
  A typical commandString is:
    12 Aug 1998 command@preventiveCare@diabetes Mellitus%%365%30

The variables and their role are:
topic=the preventive recall activity
activityPeriodicity=how often this preventive needs to happen
repeatRecallFactor=how often the program needs to nag patient/doctor
transpiredDaysActivity=number of days transpired since last preventive action
transpiredDaysNotify=number of days transpired since last patient notification
today:=today's date
lastNotify:=date last notified
  The method uses the variables and determines their values as:
1) topic:=preventiveCare@diabetesMellitus
2) activityPeriod:=365
3) repeatRecallFactor:=30
4) activityPeriodicity=36500? If true then quit protocol.
5) transpiredDaysActivity:=today−date last preventive event in Management.
6) transpiredDaysActivity GREATER THAN activityPeriodicity?
7) If true then calculate lastNotify:=last action@preventiveCare@diabetesMellitus in Actions
8) CALCULATE transpiredDaysNotify:=today−lastNotify
9) transpiredDaysNotify GREATER THAN repeatRecallFactor? If True then email patient regarding need to see doctor regarding preventive action concerning diabetes mellitus This reminder system transcends the limitation of the constraint of a single year manual diary system.
  An example of a non-medical reminder is:
    12 Aug 1998 command@exceptionReport%'update your passport'%365%14

The above reminder is for an example of a situation where the passport expires at the end of September 1999. This command will trigger an email to remind the patient/person to update his passport on the 12 Aug 1999 and will do so at a fortnightly frequency until the command is fulfilled by an equivalent action event:
    action@exceptionReport%"update your passport"

Alternatively the command can be deleted when the event has been fulfilled.

Technical Description of Medical Scripting Language Syntax

The Syntax of the Medical Scripting Language is expressed in EBNF.

This formal definition is based on Extended Backus Naur Formalism (EBNF is discussed in Programming in Modula 2 by Niklaus Wirth).

EBNF Syntax rules are defined as:
Syntax={rule}.
rule=identifier "=" expression ".".
expression=term {"l" term}.
term=factor {factor}.
factor=identifier | string|"(" expression ")" | "[" expression "]" | "{" expression "}".
  MSL is a sequence of syntax rules.
  The right hand of each rule defines syntax based on previous rules and terminal symbols.

Parentheses such as ( ) group alternate terms.
The vertical bar | separates alternate terms.
Square brackets [ ] denote optional expressions.
Braces { } denote expressions that may occur zero or more times.
A String is a sequence of characters enclosed in single or double quotes.

An identifier is a sequence of letters or digits beginning with a letter.
Example of a consultation defined in EBNF
presentation='cough'|'fever'|'jaundice'|'abdominal pain'.
links='chest x ray abnormal'|'ST elevation'|'blood test abnormal'.
unity='pneumonia'|'cold'|'heart attack'.
management='reassurance'|'penicillin'|'bed rest'|'linctus'|'patient education'.
consultation=presentation [links] unity ('reassurance'|'patient education') management.
An example of a consultation defined by the above rules is:
cough fever
chest x ray abnormal
pneumonia
reassurance
penicillin Medical Scripting Language Syntax in EBNF
MSL_file=header "|" {("|" keywordToCollection "|" {event "|"}) }"|"
header="docle_msl%" string
"id%" string
"date%" date [time] ["GMT"]
"server%" string
"content%" text|html
"contentLength%" digits
"lastModified%" date [time] ["GMT"]
keywordToCollection="#administrative"|"#command"| "#action"|"#presentation"|"#links"|"#unity"|"#management"|"images@polyline"|"images@bmp"
event=date [time] docleExpression [code%string] [imageLink] comment [accessionDetails] [status] "|"
date=dd mm yyyy.
dd=01 . . . 31.
mm="jan"|"Jan"|"feb"|"Feb"|"mar"|"Mar"|"apr"|"Apr"| "may"|"May"|"jun"|"Jun"|"jul"|"Jul"|"aug"|"Aug"| "sep"|"Sep"|"oct"|"Oct"|"nov"|"Nov"|"dec"|"Dec".
yyyy=digit digit digit digit.
digit="0"|"1"|"2"|"3"|"4"|"5"|"6"|"7"|"8"|"9".
time=digit digit ":" digit digit [":" digit digit] ["." digit digit digit] ["gmt"].
comment={string} {"~" string}.
packedString={character |"_"|"-"}.
string={character |""|"_"|"-"}.
status=+|+|+| |–
docleOperators="!"|"<"|">"|"%"|"@"|"#"|"$"|"%"|"^"|"&"|"*".
letter=capitalLetter |"a"|"b"|"c"|"d"|"e"|"f"|"g"|"h"|"I"|"j"|"k"|"l"|"m"|"n"| "o"|"p"|"q"|"r"|"s"|"t"|"u"|"v"|"w"|"x"|"y"|"z".
capitalLetter="A"|"B"|"C"|"D"|"E"|"F"|"G"|"H"|"I"|"J"| "K"|"L"|"M"|"N"|"O"|"P"|"Q"|"R"|"S"|"T"|"U"|"V"| "W"|"X"|"Y"|"Z".
character=letter|digit|docleOperator.
docleExpression={character}.
docleExpressionValueAdded=docleExpression "%" (docleExpression|packedString|""string"").
imageLink={http:www address|fileDirectory}.
code="icd10"|"icd9"|"snomed"|"otherCodingScheme"
command="command@" docleExpression "%"[string] "%" digits "%" digits
preventiveCode="preventiveCare@" docleExpression
action="action@" docleExpression [("%" "email"|"mail"|"phone"|"fax")].

The Medical Scripting Language Environment

There are currently defined more than seven special tags of the type keyToCollection:
administrative #command #action #presentation #links #unity #management #images
These tags head up collections of events described by the keyToCollection tags.
The Patient file is comprised of events organised into these collections.

Events are classified into the following types:

1) administrative
these events deal with the administrative/office aspect of healthcare. Examples are
'medicare', 'street', 'suburb', 'state', 'country', 'phone@home', email, 'phone@work', 'phone@mobile', 'dob', 'marital', 'upDate' 'markers', 'archive', 'preferredDoctor' 'pension' 'aka' 'surname' 'kin' 'workplace' 'sex' 'firstname' 'state' 'warning' 'comment' 'zip')

2) command
The commands are used to invoke the supervisory program to automate the protocols for
1) preventive health action 2) immunization 3) regular periodic prescriptions and 4) any other periodic medical protocols. The output from the execution of these protocols results in recall messages such emails, messages, a useful computer output or printed prescriptions to be issued. The command codes have the prefix 'command'.
command@preventiveCare@diabetesMellitus
command@preventiveCare@diabetesMellitus@consultation@specialist@eye
command@preventiveCare@diabetesMellitus@hemoGlobin@glycated
command@preventiveCare@diabetesMellitus@eyeCheck%%365%60 (repeat letter factor)
command@preventiveCare@lung
command@preventiveCare@weight
command@preventiveCare@alcohol
command@preventiveCare@osteoPorosis
command@preventiveCare@colon
command@preventiveCare@hyperTension
command@immunisation@infl-uenza
command@preventiveCare@cervix
command@preventiveCare@breast
command@preventiveCare@cholesterol
command@immunisation@hepatitisB
command@preventiveCare@exceptionReport%'abnormal 1ft'
command@preventiveCare@prostate
command@preventiveCare@skin
command@immunisation@tetanus
command@prescription%'digoxin(lanoxin),250mcg,1 24hi, 100 rp2'%200%200
The command@prescription is a powerful command in the sense that it automates the regular periodic prescription writing of a patient's medications. The command would trigger the preprinting of prescription scripts so that these scripts may be picked up by the patient subsequently.

3) action

Arising from the execution of the commands held in the MSL file, preventive actions such as generation of a reminder via letter or email recorded as events. Each of these events would carry a docle header beginning with the word 'action'. Each command has two numeric arguments. The first argument denotes the ideal interval in terms of the number of days that the periodic health action should be carried out. The second numeric argument denotes the number of days that are allowed to lapse before another reminder is sent.

The action type events are used to indicate the protocol for preventive health action belonging to the supervisory program.

action@preventiveCare@diabetesMellitus
action@preventiveCare@diabetesMellitus@opthamologist
action@preventiveCare@diabetesMellitus@hemoGlobin@glycated
action@preventiveCare@lung
action@preventiveCare@weight
action@preventiveCare@alcohol
action@preventiveCare@osteoPorosis
action@preventiveCare@colon
action@preventiveCare@hyperTension
action@immunisation@infl-uenza
action@preventiveCare@cervix
action@preventiveCare@breast
action@preventiveCare@cholesterol
action@immunisation@hepatitisB
action@preventiveCare@exceptionReport
action@preventiveCare@prostate
action@preventiveCare@skin
action@immunisation@tetanus The System and Method of Recall The system of recall used is based on mirroring the events in the following three OrderedCollections: Command, Management and Action. Management events of types "immunization", "preventiveCare" and "exceptionReport" all generate a collateral Action event to be placed in the Action collection. An example is the need for five yearly tetanus injections as prophylaxis of tetanus. In this instance, a tetanus shot has been given and a system of recall in five years is being set up.

The tetanus immunization shot leads to the following event being recorded in Management:

8 Sep 1998 immunisation@tetanus

This can optionally clear all previous action@immunisation@tetanus events in Action. A new action@immunisation@tetanus with the latest date is added to Action. The command event is:

8 Sep 1998 command@immunisation@tetanus%%1825%30

This command directive states that if the last immunisation@tetanus event is more than 5 years then action is to send off email reminder.

Say 5 years from 8 Sep 1998, that is around 8 Aug 2003, the supervisory program will interpret and execute the command line and find that the last immunisation@tetanus event is more than 1825 days old, an email will be sent off and the act of sending this email is recorded as the event below:

8 Aug 2003 actionRequest@immunisation@tetanus.

Say, for example, the patient failed to respond to the email reminder and no immunisation@tetanus was recorded, a second email will be sent 30 days later.

It is possible to launch more drastic action if three identical consecutive action events pertaining to the same topic are ignored, such as triggering postal mail or being listed for personal phone contact.

The event encapsulates the smallest quantum of information that may be significant in the process of healthcare of the patient.

The event is a string comprising the following subStrings tokens
1) The date token is of the format dd mmm yyyy.
2) an optional time of day token hh:mm:ss.sss and time zone.
3) a docle expression—e.g. diabetesMellitus.
4) a comment string in single quotes.
5) an optional string held in square parentheses [ ] to denote date/author of event and electronic signature of the person responsible for entering the event.
6) the last token of the event, a flag to denote active/inactive/log/suppress status of event.

The operator % means has associated value, e.g. street%'121 borg st'.

The single backslash \ is a docle operator that means 'decreased by'.

The single tilde ~ means a linefeed.

The vertical slash | is used as a delimiter of section keywords and events.

The Docle coding system has over 16,000 docle expressions. Medical scripting language is like a programming language with 16,000 reserved words. Medical scripting language is unusual in the sense that it is both a programming and a data file. Because of this programming aspect of the medical scripting file, healthcare actions can be initiated at the opportune moment to effect best patient outcome.

Privacy considerations is a big issue in medical informatics. The medical scripting language comprises means with implemented steps of downloading the patient file to a client in the network stripped of the administrative data or any obvious patient identifier, termed a headerless file to ensure privacy of medical record.

The patient identifier of this headerless file is a dynamic randomly computer generated number sequence known to both client and server, that is relevant only for the duration of the client computer session.

Control of Patient File Size/Culling of Events

Automatic culling of events or compressing of changes is set by marking the status of an event as 'negative'. This is by using the – status flag just before the | terminator for the event.

Action events that are over 2 years old may be deemed negative and transferred to archival storage to prevent overgrowth of patient file.

Archiving and compaction of files are executed by the embedded command to cull the events:

command@cull%%180%

Like all commands, there are three arguments. The first argument is cull, the second argument is 180, which means that the compaction is done half yearly. The third argument is null as there is no need to inform the patient that his file is being compacted. The supervisory program will delete all events that are termed 'negative' i.e. has a – marker just before the end of event marker |.

Another useful command is to mark those events that are prepared for culling as "negative".

command@negate@actions%%180%735

This above command will add a – sign at the end of each Action event that is 2 years old. The command will be executed every 180 days.

In one sense, the patient is like an actor and the physician is the director of the film script. The patient has to put on the 'patient role' as he undergoes surgery, being experimented on with drugs, taking tests, being filmed in the radiology lab. The SCRIPT is the main thing otherwise the patient and the physician would all lose the plot. The doctor keeps adding/ amending the script when things turn awry. But the script keeps a fair record of what the actor (patient) and the director (doctor) ought to be doing.

The key to orderedCollection tags are not necessary as the events headers (docle expressions) are already classified in the Docle medical belief system. Hence events can be reaggregated or merged. This redundancy provides safety for reconstruction of a medical record, repair of broken files and re-integration of files from a multitude of sources.

With each update of MSL, its version number is automatically updated in the administration collection of events. Each versioning event has a date stamp, the version number and the author name after the version number. The multiple versioning of events retained in the #administration collection can be arbitrarily set.

In another embodiment, tampering with the medical records file is deterred by the logging of any file changes in a changed log file.

Any change to a record file causes a new version number/ authorname change.

All changes associated with a particular medical file are written to a log.change file for that particular patient. The version number change is written to this log.change file. Say the medical file new version number is 234. Using the integrate file function on version 233 of the medical file plus the log.change for version 234, will produce a copy of medical file 234. To secure this anti-tampering device further, the log.change file can be optionally encrypted.

The medical scripting file is in ASCII Text format. The supervisory program can download to the client in plain text or in HTML format.

The headerless MSL file is a strong method of conferring privacy to patients. The headerless, administration details free, patient medical scripting language file is one where events of the administration kind are suppressed. That way, the anonymous medical events, in the event of an unintended leak to the public, will be less prejudicial to the privacy interests of the patient.

SAMPLE MSL LISTING 2 aug 1998
docle_msl%1.0
id%97649788
date%'27 aug 1998 09:03:07 GMT'
server%docle.com.au
content%text
contentLength%1240
lastModified%'5 jan 1998 19:08:17 GMT'|
|#administrative|
18 jan 1998 medicare%234567899|
18 jan 1998 firstname%David|
18 jan 1998 surname%Oon|
18 jan 1998 street%29 Darryl Street|
18 jan 1998 suburb%Scoresby|
18 jan 1998 state%Victoria|
18 jan 1998 zip%3179|
18 jan 1998 country%Australia|
18 jan 1998 phone@home%9763893
5|
18 jan 1998 phone@work%9763841
1|
18 jan 1998 phone@mobile%04109887|
18 jan 1998 email%docle@compuserve.com|
18 jan 1998 email@second%oon@connect.com.au|
18 jan 1998 dob%18 jul 1953|
18 jan 1998 marital%married|
18 jan 1998 preferredDoctor%Dr Y K Oon|
18 jan 1998 aka%Bav|
18 jan 1998 kin%Juliet Kuang|
18 jan 1998 workplace%Stillpoint Medical|
18 jan 1998 sex%male|
18 jan 1998 comment%golf chess tennis|
18 jan 1998 warning%|
18 jan 1988 version%234@authorName|
|#command|
18 jan 1998 command@preventiveCare@diabetesMellitus%365%30|
18 jan 1998 command@preventiveCare@diabetesMellitus@consultation@specialist@eye%365%60|
18 jan 1998 command@preventiveCare@diabetesMellitus@hemoGlobin@glycated%180%30|
18 jan 1998 command@preventiveCare@diabetesMellitus@eyeCheck%365%60|
18 jan 1998 command@preventiveCare@lung%365%30|
18 jan 1998 command@preventiveCare@weight%365%30|
18 jan 1998 command@preventiveCare@alcohol%365%30|
18 jan 1998 command@preventiveCare@osteoPorosis%365%30|
18 jan 1998 command@preventiveCare@colon%730%30|
18 jan 1998 command@preventiveCare@hyperTension%365%30|
18 jan 1998 command@immunisation@influenza%365%30|
18 jan 1998 command@preventiveCare@cervix%36500%0|
18 jan 1998 command@preventiveCare@breast%36500%0|
18 jan 1998 command@preventiveCare@cholesterol%365%30|
18 jan 1998 command@immunisation@hepatitisB%1835%30|
18 jan 1998 command@exceptionReport%abnormal 1ft%60%7|
18 jan 1998 command@preventiveCare@prostate%365%30|
18 jan 1998 command@preventiveCare@skin%365%30|
18 jan 1998 command@immunisation@tetanus%1835%30|
18 jan 1998 command@preventiveCare@warfarin%30%7|
action
27 aug 1998 action@command@preventiveCare@diabetesMellitus %email|
27 aug 1998 action@command@preventiveCare@diabetesMellitus@ consultation@specialist@eye%email|
27 aug 1998 action@command@preventiveCare@diabetesMellitus@ hemoGlobin@glycated%email|
27 aug 1998 action@command@preventiveCare@diabetesMellitus@ eyeCheck%email|
27 aug 1998 action@preventiveCare@lung%email|
27 aug 1998 action@preventiveCare@weight%mail|
27 aug 1998 action@preventiveCare@alcohol%email|
27 aug 1998 action@preventiveCare@colon%email|
27 aug 1998 action@preventiveCare@hyperTension%email|

27 aug 1998 action@immunisation@infl-uenza%email|
1 may 98 action@preventiveCare@cholesterol%email|
27 aug 1998 action@immunisation@hepatitisB%email|
27 aug 1998 action@preventiveCare@exceptionReport%email|
27 aug 1998 action@preventiveCare@prostate%email|
27 aug 1998 action@immunisation@tetanus%email|
|#presentation|
2 jan 1998 nose@discharge|
2 jan 1998 cough|
2 feb 1998 head@pain 6 hrs|
7 May 1998 sleep@difficultyGoingTo ++|
7 May 1998 nausea|
7 May 1998 diarrhea ++|
7 May 1998 nausea |7 May 1998 sleep@difficultyGoingTo ++|7 May 1998 diarrhea ++|
27 Jul 1998 tiredness ++|
27 Jul 1998 weight@loss 5 weeks ++|
27 Jul 1998 appe-tite*1 ++|
27 Jul 1998 skin@pigmentation*h ++|
|#links|
27 Jul 1998 s@ferritin*1|
27 Jul 1998 s@glucose=5.6 ++|
27 Jul 1998 fullBloodExamination=|
27 Jul 1998 s@sodium*1 ++|
|#unity|
2 jan 1998 upperRespiratoryTractInfection|
2 feb 1998 migraine|
7 May 1998 insomnia|
27 Jul 1998 hypo@natremia|
|#management|
1 jul 1997 preventiveCare@hyperTension 120/80|
2 jan 1998 amoxycillin@clavulanicAcid|
2 jan 1998 preventiveCare@hyperTension 120/80|
2 feb 1998 meto-clopramide|
7 May 1998 preventiveCare@exceptionReport psa*h%8|
27 Jul 1998 s@glucose|
27 Jul 1998 fullBloodExamination||

3. The PLUM Medical Belief System and Query Language System

The deluge of clinical data, often complex, can lead to unpleasant litigation as a consequence of system failure to track and evaluate the plethora of these clinical events. The problem of data overload can be met by creativity in utilising machine intelligence, but machine intelligence can only be utilised by having as its input a representation of patient status and a representation of management protocols specific to the patient. A patient file written in MSL fulfils this role.

In this preferred embodiment, the medical consultation is modulated by a piece of software called the medical spreadsheet browser. This medical spreadsheet, operating on a patient MSL file, keeps track of and evaluates the ever-increasing number of patient clinical events arising from modern medical investigations and clinical contact.

The PLUM Medical Spreadsheet is a combination of the iterative problem solving method and a unique medical belief system built along the lines of the Linnean biological system and utilising multivalent logic. The construction of this medical belief system enables clinical expertise to be built up incrementally. The angle taken by the Plum medical spreadsheet is to use the spreadsheeting process as a recordal means during patient contact. Doctors can almost afford to forget all that they learnt in medical school. As at any stage of the consultation, a discrete query to the machine can be made. PLUM uses a plurality of data cells and the iterative problem solving method, characteristic of the spreadsheet. The name PLUM is an acronym for Presentation Links Unity and Management, which is the health model used in the medical spreadsheet.

The typical accounting spreadsheet is a number cruncher and gives the accountant quick answers to "What if?" type queries. The results of this "What if?" analysis are placed in the spreadsheet cells; this sets up the conditions for the next round of calculations with no manual transcription. The accountant's electronic spreadsheet is prodigious for tasks that require repetitive work with a hand held calculator. Hitherto, there is no such equivalent spreadsheet in the medical domain. With PLUM, during a client encounter, there is the capability of:
  allowing data entry and recording,
  performing "What if?" calculations pertaining to client diagnosis and management, with the results placed in cells for the next round of evaluation, and
  features such as scrollable worksheets which can be saved.

PLUM is used in a real or simulated patient or client encounter environment. During a patient encounter, the clinician needs to record the clinical details and constantly makes evaluations of clinical problems, resulting in treatment in the event of a diagnosis. In the event that no diagnosis is made, further investigations are instigated. PLUM facilitates the recording of clinical data while at the same time using the same worksheet to provide computer evaluation of clinical status with resultant guidance regarding problem analysis, investigations and treatment. The motivation of PLUM is to introduce the spreadsheet metaphor into clinical medicine. There were at least two main barriers that needed to be surmounted to attain such an invention. The first was coming up with a replacement for the number system used in conventional spreadsheets. PLUM uses a word-based coding and medical belief system modelled on the Linnean classification. In this system a medical condition such as "gout" is a medical species with its own phylum, class, order, family and genus. The second barrier was surmounted by finding a suitable homogenous clinical data model of patient health status at the local encounter and global levels.

The traditional model of the encounter is called SOAP for Subjective (symptoms), Objective (physical signs), Assessment (what the doctor thinks of the whole consultation) and Plan of management. In the old medical model, the patient global status is a list of active/inactive problems. The homogenous model used by PLUM is the Graduated Discrete Definition Model which allows the clinical encounter data to be viewed in the same framework as the patient global status. This new model overcomes all the shortcomings of the traditional medical record where the encounter is disjointed from the patient's global status. PLUM provides the clinician with a spreadsheet tool for use in patient care to effect efficient diagnosis, management and data recording. There is also a paper equivalent to the medical spreadsheet which forms the basis of an effective manual/hybrid medical record system. The input and output of the medical spreadsheet process are based on the cells of the spreadsheet during a real or virtual patient encounter. As the input and output arising from the patient evaluation are all cell based, this provides the powerful paradigm of iterative and hypothetical type problem solving. Applying the same spreadsheet metaphor, the pages (or worksheets) of this medical spreadsheet can be scrolled back and forth and get saved for future reference. This clinical data model used in the medical spreadsheet supports a logical framework for the recording of the clinical encounter and displays cumulative patient data in the same format as the clinical encounter. In this Graduated Discrete Definition Model, the classification of all clinical data uses one main criterion, which is the degree of definition of a clinical datum in terms of readiness for medical treatment and/or prognostication.

With such a classification framework, at one end of the scale there would be the not-yet-defined clinical data, such as a clinical symptom or sign; these clinical data items do not have the degree of definition necessary for treatment or prognostication. At the other end of the spectrum, we have the well-defined clinical data, such as a diagnosis which has a clear prognosis and treatment. There can be one or more intermediate categories positioned between the not-yet-defined and the well-defined categories. The preferred option of PLUM is an intermediate category called the about to be defined category. To complete this classification model, there is an additional category to include all extrinsic patient clinical data comprising treatment and investigations. The tetrad version of the Graduated Discrete Definition Model is called PLUM. All clinical data to describe the patient status and patient management is classified into the four categories of:

Presentation—this comprises all not yet defined clinical data such as symptoms and signs, Links—this comprises all about to be defined clinical data such as the abnormal test results and provisional diagnoses made by the doctor; these entities are not specific enough for treatment and/or prognostication but better defined as compared with the not yet defined data, Unity—this comprises all well defined clinical data of the clear diagnosis type where there is specific treatment and/or prognostication, and Management—this comprises laboratory and radiological investigations, drug treatment, procedures and process of care.

PLUM represents the four categories of the tetrad version of the Graduated Discrete Definition Model. The clinical encounter form has four cells, representing the four categories of PLUM. The Presentation cell is reserved for not yet defined clinical data. The Links cell is reserved for about to be defined clinical data. The Unity cell is reserved for well defined clinical data. The Management cell is for clinical data relating to treatment and investigations. The PLUM model provides the framework for the spreadsheet. The Graduated Discrete Definition Model, of which PLUM is the tetrad implementation, is congruent with the underlying logic of the doctoring process, which is the processing of unclear clinical information to resolution in the form of a well-defined diagnosis. This is followed up with treatment, or investigation if resolution is not possible. The "What-if?" query is launched from the drop-down menu, of which there is a choice of over 50 useful types out of a possible 225 basic permutations. Typical queries of the medical spreadsheet would be:

given symptoms and signs, show possible diagnoses, given a set of possible diagnoses, symptoms, signs and laboratory test results, show only diagnoses that conform to available data, and given a list of diagnoses, show diagnosis that can unite several diagnoses.

After each computer-assisted evaluation, the worksheet is updated and the worksheet page number is incremented by one. The PLUM worksheet on the screen is called a page. It depicts a real or hypothetical image of the patient status and can be saved and recalled.

It was the congruent classification of disease entities, akin to the building of a belief system framework, that allowed the medical belief system to be viewed using the spreadsheet metaphor. PLUM is relevant to any problem domain where the problem solver needs to arrive at a diagnosis given a set of indeterminate data. The knowledge domain that almost mimics the medical domain is the legal field, and an equivalent theory for legal problem solving in the spreadsheet form also exists (patent pending). PLUM represents a new class of software—non-numerical spreadsheets. While a patient MSL file can be downloaded and read on any internet browser, the benefits of writing the patient electronic medical record in MSL is that one can do iterative problem solving of the patient problems. The implementation of a medical spreadsheet operating on files downloaded and then uploaded to the internet can be achieved via at least four methods over the world wide web:

A. Using a generic internet browser, the cells of the spreadsheet are painted by a server program that generates the requisite HTML text to update the screen.

B. Use of a plug-in technology such as JAVA or Smalltalk.

C. Purpose built from scratch internet browser incorporating features of the spreadsheet interwoven into the internet browser.

D. Outside the world-wide-web, the MSL patient file structure would be ideal in a distributed computing environment such as distributed smalltalk and even as a remote window session.

Technical Description of the Medical Spreadsheet Browser as a Web Application Running on Generic Internet Browsers To start the medical spreadsheet browser:
1. Start the web browser. This may be Mosaic, Netscape or Internet Explorer.
2. Using the web browser, request the following URL: http://www.hostMachine/launch/plumSpreadsheet
3. The browser sends the request to the server hostMachine.
4. The hostMachine uses default resolvers, the path 'launch' will cause the execution of the program plumSpreadsheet on the host machine. In this embodiment, an instance of class plumSpreadsheet, a user interface session of the medical spreadsheet, is created. Sessions make it possible for multiple users to have concurrent use of the server supervisory program.
5. The server will seek verification of user and password.
6. The patient file written in medical scripting language is retrieved.
7. The plumSpreadsheet session main menu will have choices for global log, global inactive or global active displays, an encounter spreadsheet form and save and cancel buttons.
8. Say the plumSpreadsheet encounter is chosen; the session will, instead of splashing a screen with a plurality of cells on the screen and a pick list, convert the panes and text into a hypertext Markup Language (HTML) document which is despatched to the browser for display.
9. After entries are made in the Presentation, Links, Unity or Management panes, then if one of the queries is activated, a submit request and the data in the spreadsheet in the cells will then be despatched from the client browser to the supervisory program.
10. The supervisory program evaluates the spreadsheet query, produces an appropriate response and then despatches the answer back in HTML format to the client.
11. Go to 9.

Docle Expressions

The Docle medical coding, classification and belief system.

Any medical decision support system requires in the background, a belief system comprising a basic set of assumptions. The alphabetic Docle system unifies coding, classification and knowledge representation in medicine. With Docle, the codes are mere keys to the medical belief system. Medical entities are classified as species and placed in a Linnean hierarchy much like a species such as Homo Sapiens in biology. For instance, the liver object at the level called ORDER, knows all its associated diseases, symptoms and signs. The Docle coding, classification and medical belief system appears to be an efficient approach to data representation in medicine. There is a spectrum of options in data representation in medicine, ranging from natural language at one end of the spectrum, to the other extreme of representing medical entities as numbers. Docle is an all but natural alphabetic language suitable for machine processing. The Docle framework has equal facility for 'lumpers' and 'splitters' of clinical codes.

Each of the thousands of Docle medical objects are related to one another in a linnean hierarchy as in biological classification. The Docle approach is to recycle lexical patterns and judicious use of operators to make powerful expressions. Hitherto numeric coding systems such as ICPC and ICD are designed for epidemiologists and statisticians. The challenge in medical informatics is to encode medical data for day to day patient care, clinical decision support, transportable medical records and intelligent medical systems. These next wave projects have severely strained the old numeric coding paradigm. Next wave coding schemes will likely be alphabetic and will incorporate attributes of medical belief systems. A code for a symptom will be linked to associated organs. The classification system comprises the following phyla or chapters: disease diagnoses, symptoms, signs, reasons for encounter, diagnostic imaging, diagnostic non-imaging, treatment procedures, and therapeutics. The Docle coding and classification system has been designed to solve the following problems 1) a coding system in medical informatics 2) a method to achieve standardization of medical abbreviations 3) a medical belief system that parallels the Linnean model in biology suitable for the organization of medical knowledge and 4) a medical belief system suitable for the design and implementation of sophisticated medical decision support systems. The Docle health classification system has drawn the two strands of biology and medicine together in that they follow the Linnean model of classification.

Aspects of Docle

1) Docle is a belief system modelled on the linnean biological classification system.

The linnean biological framework has been stable for over 200 years. There is no coding and classification problem in biology. By modelling on this framework, the full potential of medical coding and classification is unleashed with the Docle framework. Medical entities are classified as species and placed in a hierarchy much like a species such as homo sapiens. Every one of the over ten thousand Docle medical objects are thus related in a congruous framework. For instance the liver object at the level called ORDER knows all its associated diseases, symptoms and signs. The Docle health classification system has drawn the two strands of biology and medicine together with a common linnean model.

2) Backward compatibility and future potential.

The choice of coding system in the field of medicine must in a sense comprise at least the functions found in the three buttons one expects in a video recorder. The buttons are PLAY, REWIND and FAST FORWARD. The linnean Docle coding and classification system which is demonstrably efficient—has those three functions. Docle is in an advanced stage of mapping to ICD9 and ICD10. In that sense it has a rewind function. Docle has the expressivity of natural language, and yet the precision of numeric coding, and can be mapped and made backward and forward compatible to any coding system. The fast forward function of Docle is its intrinsic strength in knowledge representation. The embodiment of such a knowledge tool using Docle is the medical spreadsheet.

3) Simplicity of design framework, clarity of embodiment.

Docle is a linnean, hierarchical system with multiple inheritance. All that means is that Docle combines some of the ideas of object oriented design and the linnean biological classification of Carolus Linnaeus, to tackle the issues of medical coding and classification. The problem in medical coding and classification is comparable to the challenge of covering all the surface area in say the bathroom, with band-aids with either no overlap or controlled overlap. Certain surfaces in the bathroom, such as the taps and toilet bowls are difficult to say the least. This metaphor describes the need to code for every symptom, sign, disease, investigation and investigation result in clinical medicine. Another way to look at the medical coding challenge is to imagine the work being similar to a biologist classifying thousands of problematic species like the platypus.

The linnean biological framework comprising phyla, class, order, family and species is an ingeniously suited framework, after modifications, for classifying medical objects. Docle is different in that it is totally alphabetic and uses primary, secondary and tertiary keys to access "objects" that hold the linnean properties of each medical object. All these objects are linked together in a congruent 'belief system'. There is no more mapping of diseases to meaningless numbers. Docle breaks free from the restrictions of multiaxial coding such as the system used in SNOMED. Nothing stays the same in medicine. The Docle framework is designed for expected constant change and improvements in our understanding of medical science. With Docle, the band-aids come in various shapes and sizes in order to cover everything in a congruent manner. One can even imagine tiny band-aids that are arrayed in the manner of jigsaw puzzles to make up the complete area of a large irregularly shaped band-aid. Certain parts of the bathroom are covered with up to six or seven layers of band-aids which are meticulously cut, measured and catalogued. Each band-aid, no matter how small, knows its relationship to every other band-aid in the bathroom.

Embodiments of Docle:

The primary key for colles fracture is fracture.radius@coll-es, the secondary key being frac.radi@colles (the Docle algorithm automatically generates a standard abbreviation), while the tertiary or alias key is collesFracture.

There is also fracture.radius@galleazi. Now these two entities have as their genus fracture.radius^. The entry for colles fracture was a late entry. The previous 'best' code had been fracture.radius (frac.radi), this "band-aid" covered a lot of territory, fracture.radius@coll-es is a species form of the genus fracture.radius. A medical entity often has several genuses (multiple inheritance). This is akin to a small band-aid overlaid by several large irregularly shaped band-aids. The other good name for genus is UMG or useful medical grouping. Remember Docle is linnean, hence it looks better for use terms like genus and family order where the hierarchy is already predetermined. With colles fracture, if you had coded with fracture.radius, it would not matter. In the future when you search for colles fracture, the search engine would recruit all the species associated with the genus or UMG called "fracture.radius", as that is the UMG that fracture.radius@coll-es also belongs to. The issue of deprecation of codes is important. With Docle, the scheme used to manage codes that are no longer used is termed Graceful Deprecation (see below).

Updating Docle is easy. A hypothetical example is that of an *eschericia coli* strain causing an outbreak of food poisoning in Melbourne. The microbiologists in Parkville have identified a new species they have christened the 'Melbourne' strain. Coding this in Docle is straightforward:

infection<eschericia@coli@melbourne
  ->infe<esch@coli@melb as there is in historical precedence, a whole series of infection<escherichia@coli@subspecies.

The operator characters are for "located at", @ for associated with and of course > and < meaning "leading to" and "due to" plus other useful operators.

Now compare the above with the complexities of ICD9 and ICD10 below, where a lifetime of study still will not make you competent in coding. Life is too short for living with numeric coding systems with self inflicted complexity.

4) The KISS principle

Docle is simple and efficient, it is totally alien to the look and feel of numeric coding systems such as ICD9 and ICD10.

Below is an example of the trauma of working with ICD-9 and ICD-10 coding:

ICD-9-CM codes
  910.0 Abrasion or friction burn of face, neck or scalp except eye, without mention of infection
  910.1 Abrasion or friction burn of face, neck or scalp except eye, infected
both map forward historically to ICD-10-AM code
  S00.01 Superficial injury of scalp, abrasion.

However the AR-DRG grouper software code 910.0 groups to DRGs 492-494 Trauma to the skin, subcutaneous tissue & breast, while code 910.1 groups to DRGs 489-491 Cellulitis. The two ICD-9-CM codes group to different DRGs but map historically to the same ICD-10-AM code (S00.01). To maintain congruency, a patch is needed. The ICD-9-CM codes needs to be logically mapped to maintain the DRG groupings. A logical map for 910.1 to ICD-10-AM code is L08.9 (local infection of skin and subcutaneous tissue, unspecified is needed). The above examples show that when codes transcend multiple anatomical sites, pathophysiological processes and with the mixing of medical idioms—this inevitably leads to future incongruencies. Constructing medical belief systems for decision support with such a numeric scheme is a material challenge.

5) The Ostension problem—properties, not pointing

One significant difference between Docle and the traditional numeric approach to medical coding and classification involves the philosophical issue termed the "ambiguity of ostension". The inflection point in the evolution of medical coding systems is the grappling with the issue of ambiguity of ostension. Ambiguity of ostension is a topic found in basic philosophy text books. The numeric coding schemes use 'pointing' while Docle uses the concept of 'properties' or behaviour. Pointing leads to a conundrum referred to in philosophy as the ambiguity of ostension or the fallacy of mere pointing. In the classic sense this happens when we try to extend the vocabulary of a young child. The parable of the inquisitive child (as covered by Gareth Matthews in 'Philosophy and the Young Child') asking of the meaning of the French word 'La Table'. He was not satisfied about the father merely pointing to a table. He asks 'How does one know that the pointing is not at the table top or the colour of the table?'. Looking up the meaning of a word in the dictionary is not helpful when it just points to a bigger unknown word. Looking up a key in a numeric coding scheme leads to an obscure numeric code. A grand scheme like UMLS is like looking up the meaning of a word and being told that the meaning of that word in Swedish, German or Swahili. Augustine in De Magistro resolved the problem by stating that the meaning of a word say "bird-catching" is demonstrated by a bird-catcher doing his thing. Augustine goes on to say that an observer intelligent enough will eventually catch on to what bird-catching is and hence what bird-catching means. Meaning is derived from the properties or aspects of the behaviour of 'bird-catching'. In a sense, the Docle coding scheme comprises objects with behaviour. Each Docle object is evaluated by its 'behaviour'; its utility is derived by leveraging on its relationships to other Docle objects. It is obviously much easier for the software implementer to implement his decision support using a coding scheme based on properties and behaviour, rather than a pointing system. An alphabetic scheme like Docle is much easier to support. Over a weekend, urgent requests for 50 to 100 items could be coded in Docle. Which coding scheme can give that sort of turnaround? Docle can. Remember the fallacy of ostension. The prayer for every medical informatician is "Give us each day more properties rather than more pointing in our coding systems and forgive us for the trouble we have caused with the codes we have deprecated." At 16,000 items identified and classified over the past 10 years, the hack work for Docle is largely done.

6) Decision Support

The cogent reason for digitizing medical data is machine facilitated decision support. Docle has demonstrated its sheer suitability for decision support in the form of the PLUM MEDICAL SPREADSHEET as documented in the PCT application.

7) Universal Transportable Medical Record

Any universal transportable medical record initiative without a defined medical coding system is like a vehicle without wheels. Using Docle, this transportable active medical record moeity is termed DocleScript which forms one of the three components that form the basis of this patent application.

8) Size

Docle is not too big, that is a plus. UMLS is big, maybe too big. This applies to the other numeric coding schemes. Big is not necessarily better. Who needs 60 terms to describe candida infection? Two or three are enough. A big coding list will just slow the pick list. The optimal size should be large enough to fulfil our needs and no more. Remember properties and not pointing! When people boast about their 400,000 terms list, it is more hubris than logic. Resolution matters, not size—a poor resolution photograph if blown up will only show more fuzziness. Just like the photos captured on a Kodak box camera, no matter how you enlarge the print from the box camera, the photo resolution is still a disappointment. Mapping four fuzzy numeric coding systems gives you a fuzzy numeric system four times bigger. There is so much hubris and hype about the existing numeric "official" codes that we need our eyes opened to see the emperor's clothes for what they are.

9) Splitters versus lumpers; differentiation versus integration

The perennial conundrum faced by the WHO ICD classification body has always been the issue to lump codes together or to split them into more specific codes. With Docle, we can split and lump at the same time. We can differentiate the various species and subspecies of "DiabetesMellitus", but the differentiated species know their memberships in the various genuses. We need complexity but with complete integrity. We need to split and lump at the same time. This differentiation/integration design creates outward simplicity for the end users who are only interested in real life medical entities and not some abstract artificial codes that span disjointed anatomical areas and pathophysiology as in the numeric code examples.

10) Variable versus computer constants

One of the biggest differences between Docle and the prior art of Read, ICD, SNOMED and ICPC is that Docle uses the computer variable concept while the rest of the field are implemented like computer constants. A variable is like a container. This container in Docle, called a Docle object, can be accessed via primary, secondary and tertiary keys. The three types of keys are equivalent in the sense that they all point to the same container with its stored methods and data. Inside the container is the belief system about the object. While the name of the variable is fixed, the contents of the variable may vary over time. Docle makes use of the concept of separation of the belief system data from the key code itself. This separation of the properties to the code key itself provides Docle with unparalleled flexibility to expand and mutate with the growth of medical knowledge. The key, be it primary, secondary (Docle abbreviations) or tertiary (aliases)—all leads to the same medical object with its stored behaviour. Medical advances will lead to gradual adjustments to the behaviour of the medical object. It is hard to envisage the need to change species names such as rheumatoidArthritis or diabetesMellitus.

11) Number codes is not a viable belief system

The linnean System in biology is a viable belief system that is alive, moving on with the advancement of biological knowledge. It is a framework or road map to the realm of biology. The gap in the linnean framework excites the imagination of the biologists about missing links in their knowledge. It is a powerful method of cognating the knowledge that is being accumulated. This yearning for classifying and cognating medical knowledge was expressed in the preface of the ICD 9 manual, but it was just a yearning.

12) Granularity problem and the Genus chunking solution.

The granularity problem is familiar with anyone attempting to write a decision support program in medicine. An instance of this problem is the flagging of the disease/drug interaction between the beta-blockers and diabetes mellitus. It would be tedious, inefficient and prone to error to try to pick up every specific type of beta-blocker interacting with every variation of diabetes mellitus. An example of the beneficial effects of chunking into genus level is the case of diabetes mellitus. Chunking up of the three variants of diabetesMellitus:
diabetesMellitus@gestation,
diabetesMellitus@insulinIndependentDiabetesMellitus,
diabetesMellitus@nonInsulinDependentDiabetesMellitus
into a genus called diabetesMellitus, allows the common behaviour to be stored in the diabetesMellitus genus object.

Likewise we can chunk up the therapeutic species of propanolol, atenolol and metoprolol into the medical genus betaBlocker. An adverse drug-disease interaction is flagged when the two genuses of betaBlocker and diabetesMellitus are combined. A new beta-blocker will inherit this interaction behaviour, as soon as it is tagged, as belonging to the genus of betaBlocker in its container holding its belief system.

13) Why choke on number codes when Docle is a feast in verse?

Numeric coding schemes look like this T-2800 M-44060 E-2001 F-03003 for pulmonary tuberculosis with granuloma.

While some Docle codes for chest pains look like these:
chest@pain/neck@move
chest@pain/food
chest@pain/respiratory
chest@pain%min where the / operator means increased or aggravated by and the % operator denotes quantification.

14) Docle carries with it a free and unified medical abbreviation standard.

The abbreviation is the computer generated secondary key. For example carcinoma located at thyroid is coded as carcinoma.thyroid and the secondary key/abbreviation is carc.thyr 15) Code shear technology Docle is built up of words joined by operators, much like an internet address. Coded entities are modified by aspects such as laterality, acute, chronic, simple, compound, complicated and male or female. The modifiers are added to the main code by the clicking of buttons. The & character is the shear or modifier operator, an example is the code fracture.femur&rightHandSide&simple. During processing the substring &rightHandSide can be sheared off to return the basic code: fracture.femur.

16) Best Practice by stealth

Evidence Based Medicine (EBM) can be encoded inside the Docle object. Each disease docle object can have a list of ranked recommended treatments and a list of ranked investigations. Adoption of a Docle type coding system will achieve EBM by stealth.

17) Anatomical belief system behind the Docle framework

All Docle objects are linked together to form a viable and congruous belief system, even in the anatomical sense. The need to map every Docle object onto an anatomical framework has thrown up a previously unnamed body organ. It detected a gap in its anatomical hierarchy. The anatomical locations scrotum and testis has a missing superclass, Docle has christened this organ the tistum. The Docle for tistum is tist which has as its subclasses scrotum and testis. Docle is the first medical coding system with an official term for balls. A disease entity that involves a finger can trigger the message that the hand is involved. This part of the anatomical belief system behind the Docle framework.

18) Docle has been subjected to the duress of actual use

Docle is undergoing stepwise refinements with constant usage. This is in actual clinical trials in the medical community in decision support and in clinical record keeping.

19) Graceful Deprecation

All coding schemes get into the sticky situation of having to dispose of superseded codes. There are a variety of schemes to deal with these superseded codes. One way is to publish a list to say these codes are no longer valid. Another way is to use an autogenerated number to represent a code. This autogenerated number once used, is never recycled. The problem is that your electronic medical record will be studded with all of these autogenerated numbers. To make sense of these autogenerated numbers, one will need a lookup table. Making sense of the relationships among these autogenerated numbers will require great ingenuity and effort. There is a softer and gentler approach to deprecated codes employed by Docle whereby the bottom-line worst-case scenario is being saddled with a human readable and understandable Docle code or expression that makes clinical sense. With Docle, a new scheme for handling deprecated codes termed Graceful Deprecation is introduced. In this scheme all deprecated codes are not deleted. They are tagged to be deprecated codes and are incorporated as tertiary keys to the Docle belief system. Hence, on looking up a Docle code in the belief system, if the key is not found, the system will next assume that it is a deprecated code and will reconcile it as a deprecated tertiary key to access the system. This scheme is made possible by the fact that all tertiary keys are mapped to an objective external reality that is matched by clinical practice.

20) The Doclescript Plum Medical Spreadsheet Browser

The Docle concept is best explained by diving into the browser. Just like it is hard to explain about the world wide web; it is much easier to give someone an internet connection and a Netscape browser and let him roam.

The Docle PLUM browser is a multi-paned application that shows to advantage the Docle/DocleScript framework. All medical entities are displayed on a listing pane. Selection of a medical entity will cause it to be displayed in one of the four panes. Medical decision support queries are allowed and allow iterative problem solving. The contents of the spreadsheet can then be saved as a record of the encounter. This allows integrity of decision making while recording a patient encounter.

Technical Description of the Docle Linnean Classification System

The Docle framework is a classification system for the medical domain based on the Linnean model. Classification by the direct transposition of the medical domain into the biological model, of course does not work, as the framework is not fully compatible. For that to happen, there are three prerequisites. Firstly, we need the equivalent of the binomial nomenclature. This nomenclature must be a powerful and standard way of describing medical entities. Secondly, we need to completely rework the Linnean hierarchical levels and introduce new definitions for the various levels. Thirdly, we need to create new rules for the classification process. Instead of Latin names, we have a structured medical descriptive language in Docle. In the majority of cases, Docle names are names of medical entities that are straight out of the medical textbooks. Occasionally they may look like someone's internet address. Docle uses the concept of the species name, being the primary KEY to a medical object, also called a Docle object. Hence Docle is a classification of medical objects. The medical object holds information that refers to memberships of taxa, pointers to species in lower levels of hierarchy and its own level of hierarchy. That way, as medical science progresses, the medical object is updated but the key remains stable. As there is no need to assign numbers to entities that are not numbers, species names are alphabetic. The problem is therefore straightforward. We have to 1) Identify all the species (or subspecies thereof) of medical objects 2) Assign to each species named, an object which is a data repository regarding its memberships of taxa and other information and 3) Classify them into a logical framework satisfying the requirements of all manner and types of health workers. This is important, as previous coding systems were designed for the medical statisticians and certainly not for the information scientist who is developing applications such as a) decision support in a clinical setting and b) paperless medical records.

The Docle Framework

Docle models the ideas of biological classification started by Linnaeus in the 1750s. One of the central tenets of biological classification is the concept of the species. The other tenets being the hierarchies and the concept of the taxon (plural taxa). A taxon is a group with shared values in each hierarchy. Species identification is half the work, while the other half involves placing the species in the right taxon in the right hierarchy.

The system of classification in Docle is based on the above framework with major modifications.

The main deviations from the Linnean model are:
1) There are more hierarchies defined below the species level. There are the subspecies, subsubspecies subsubsubspecies and subsubsubsubspecies levels already defined.
2) A species or any of its subclasses can have membership in any number of taxa at any level. This is the multiple inheritance feature of Docle.
3) The corollary of the above is that a species may have no membership of any taxon at any specified level.
4) As implemented in Docle, a taxon knows its membership. A species knows who its subspecies, subsubspecies, subsubsubspecies and subsubsubsubspecies are, if there are any.
5) The taxa at the next level down of the hierarchy does not need to be descendants of a taxon at the current level.
6) The entity to be classified is held in a Docle object (also referred to as a medical object). The name of the object becomes the key to the object. There are three types of keys to these Docle objects. The primary key is the complete key that can look like a textbook name or an expression that looks like an internet address. An example of a primary key is diabetesMellitus. Note the absence of a space between diabetes and mellitus. The secondary key is computer generated and is an abbreviated version of the first using the Docle algorithm. Hence the secondary key is diabm. A secondary abbreviated key is useful in that doctors like to communicate in a shorthand manner when possible. It is also a subtle method to get doctors to standardise on abbreviations. The tertiary keys are the nominated aliases of the entity. To summarise, in the case of diabetes mellitus, the primary key is diabetesMellitus; the secondary key is diabm and the tertiary keys are the aliases: diabetes, sugar diabetes.

The Hierarchies in Docle
1. Kingdom—there is only one taxon located at this hierarchy. It is named Objects Medica. Objects Medica holds all medical objects and all objects of medical thought.
2. Phylum—the taxa are:
   a) Medical Administration
   b) Symptoms Signs
   c) Diagnostic Non Imaging
   d) Diagnostic Imaging
   e) Procedures Process Of Care
   f) Therapeutics
   g) TAMTAP—(Thinking About Medical Thinking And Practice)
   h) Reason for encounter
   i) Clinical Domains 3. Class—the taxa are the various clinical fields in medicine. The groups are Adolescent Health, Blood, Cardiovascular etc.
4. Subclass—is reserved for the exciting frontier of genetic medicine. With the complete mapping of the human genome, gene locations/regions can be linked to specific medical syndromes. For example the HLA class II genes are linked to IDDM. We can use taxa such as a) X-linked or b) Y-linked. We await a uniform nomenclature for gene maps.
5. Order—the taxa are named anatomical locations and organs.
6. Family—the taxa here are for the biochemical and physiological bases of disease. This can be at the molecular and cellular level. Examples of the groups here are a) Disorders of lipid metabolism b) Disorders of the prostaglandins c) Disorders of nitrous oxide metabolism d) Disorders of heat regulation e) Disorders of the mucopolysaccharides f) Disorders of cell membrane transport. The subfamily hierarchy is reserved for taxa related to DRGs and Casemix.
7. Genus—a taxon at this level is a larger concept and holds from 11 to 200 species. Examples of taxa are a) valvular heart disease b) arrythmia c) fractures d) benign neoplasm e) malignant neoplasm f) intermediate neoplasm.
8. Superspecies—a taxon at this level is a concept that holds 2 to 10 species. An example of a superspecies is fracture of the femur. It is not specific enough for treatment and prognostication, it contains several species.
9. Species—The root word is the Latin specere which means "to look at". At the species level the medical entity is real and can be looked at or experienced by the patient/clinician. A species belonging to the phylum Clinical Domains is a characteristic syndrome with clinical features generally known. Often there is knowledge about its aetiology. There is knowledge regarding diagnosis by clinical and/or non-clinical methods. There exists in many cases a knowledge of its natural history. There is associated a system of management of this syndrome and in many cases methods of prevention. A diagnosis at the species level or better is required for specific therapy. Examples of a species are diabetesMellitus, fracture.femur@neck and acidosis@metabolic. Species belonging to phyla other than Clinical Domain are non-abstract entities such as cough, chest X ray, or a swelling located at neck.
10. subspecies—A differentiated type arising from species, it suggests more specific treatment and prognostication.
11. subsubspecies—A more differentiated type arising from subspecies.
12. subsubsubspecies—A differentiated type arising from subsubspecies.
13. subsubsubsubspecies—A differentiated type arising from subsubsubspecies.
14. subsubsubsubsubspecies . . . .

A Case Study—Classification of Fractures Involving the Neck of Femur.

The primary keys are followed by its secondary keys.
The production of these secondary keys are automated by the use of the Docle algorithm
kingdom: object medica
phyllum: clinical domain
class: musculoskeletal
order: femur
family: disorder of bone metabolism
genus: fracture.femur—frac.femu, fracture—frac
species: fracture.femur@neck—frac.femu@neck
subspecies: fracture.femur@neck@pertrochanteric—frac.femu@neck@pert
subsubspecies: fracture.femur@neck@pertrochanteric@avulsion—frac.femu@neck@pert@avul Docle is human readable and is more suited to input validation. For instance the dot operator means "located at", validation routines will make sure that the referred site is a valid anatomical one. Docle is human readable, hence it is more suited for mission critical tasks because the nurses and doctors can visually vet for the correctness of computer data. The Docle codes are both human and machine readable, these codes are actually embedded in each of the events in DocleScript. With the changing pattern of health care delivery and a highly networked society, the advantages of a unitary system like Docle that can span across the various departments and specialities would be obvious. The statisticians can work at the genus level. The primary provider at the species level and the specialists and research scientists can work lower down at the subspecies or subsubspecies level. By the application of a human readable, character based primary Docle code, which the resident medical officer enters from a pick list in the patient electronic record—that piece of data capture by the resident medical officer or the staff nurse meets the data requirements for i) the day-to-day patient recording ii) medical decision support and iii) administrative purposes.

The Algorithm

The algorithm itself is of general applicability. An argument can be put forward for the use of the Docle algorithm as a good programming aid—as a naming convention of program variables, procedures, functions and computer commands. A Docle type exercise may even be relevant in the general print media beyond the medical domain. At the flight information displays, one can imagine MELBN, SYDN and NEWY to mean Melbourne, Sydney and New York. The abbreviations for Austria and Australia would be AUSR and AUSRL respectively.

The Docle Algorithm Description Definitions
i) The output of the Docle Algorithm is called a Docle word.
ii) Each Docle word is comprised of the printable ASCII characters.
iii) Each Docle word is unique in its meaning.
iv) No spaces are allowed in a Docle word.
v) The characters a e i o u y are defined as Docle vowels. The rest of the character set are consonants by definition.
vi) Docle words are case insensitive.

Suggestions
i) Docle words referring to the same medical entity are avoided. Where possible, combine existing Docle words to refer to a new medical entity rather than create a new Docle word.
ii) Eponymous entities are avoided if possible.

Transformation Rules

The medical expression is subjected to the initial process of fragmentation. A word that contains a hyphen is broken up into two words. Words that are constituted from multiple subwords are fragmented into the original source words, e.g. electrocardiography is fragmented into electro cardio graphy, X-ray is X ray. After fragmentation the word(s) are treated according to the three different possibilities of the one word, two words or three and more word situations.

Medical Terminology Comprising a Single Word i) A word that has four or less characters is left unaltered.
ii) The Docle word is derived by concatenating the derived prefix to the derived suffix.
iii) The prefix is defined as that contiguous group of initial characters of the source word. Scanning from the left, the prefix starts from the first character and ends at the first consonant after any vowel. In the event of the prefix being less than three characters long, the first three characters are made the prefix.
iv) The source word, minus its prefix, is termed the remainder.
v) The suffix is a group of characters derived by scanning the remainder from right to left. The immediate consonant after any vowel that is encountered is added to the group, until the whole remainder is scanned. The consonants thus obtained are placed in the order as found in the source word. In the event that this scanning process yields zero characters, and that the prefix is only three characters long, then the first character of the remainder is made the prefix.
vi) In the event that the result of concatenating the suffix to the prefix is six or more characters long, this result is passed through the algorithm again.

Medical Terminology Comprising of Two Words

The first word is subjected to the same treatment as the single word terminology case. The product is then concatenated to the first character of the second word. Any mapping conflict is resolved by using alternate medical expressions as the source.

Medical Terminology—Three or More Words

The first characters of each and every word are concatenated together. Any mapping conflict is resolved by using alternate medical expressions as the source.

Medical Terminology—Two or More Words where Part of the Expression can be Represented by a Docle Word The first word of the expression is replaced by its Docle word. The first characters of the remaining words are concatenated with the Docle word.

Comment

The design goal of aiming at preponderance of four character length Docle words is met. The second pass mechanism sets an upper bound of six character for single word derivatives. Examples are as follows:

One Word (Get the prefix, then the suffix and then concatenate.)

| migraine | >migr_aine | >migr |
| abdomen | >abdo_men | >abdm |
| femur | >femu_r | >femu |
| humerus | >hume_rus | >hume |
| pain | >pain | >pain |

Two Words (First word subjected to transformation as one word case. The product is concatenated with the first character of the second word.)

| diabetes mellitus | >diabetesMellitus | >diabm |
| x ray | >xRay | >xr |
| herpes zoster | >herpesZoster | >herpz |

Three or More Words (The first characters of each word are concatenated together.)

| acquired immuno deficiency syndrome | ->aids |
| electro cardio graph | ->ecg |
| transient ischemic attack | ->tia |
| upper respiratory infection | ->urti |

Operators and Symbolic Shorthand

The Docle operators are designed to give the Docle language the power of expression not seen with numeric coding of data. The operators allow the user to combine two or more Docle words together to form Docle expressions. There is provision for more operators as there are more than a dozen printable ASCII characters still unused. There are, as currently defined, a dozen operators and several shorthand symbols, the primary keys are followed by their secondary keys in brackets:

| Operator | Meaning | Example of Use |
|---|---|---|
| . | LOCATED AT | tuberculosis.kidney (tube.kidn) is read as tuberculosis located at kidney. |
| > | LEADING TO | back@pain>buttock (back@pain@butt) is read as backpain radiating to buttock |
| < | DUE TO | pneumonia<virus (pneu<viru) |
| @ | APROPOS | detachment@retina is read as detachment apropos/ associated with retina. |
| : | DESCRIBED AS | pain:dull is read as pain described as dull. |
| $ | DATE | fracture.humerus$'2 feb 1988' is read as fractureof humerus date being 2 feb 1988. |
| & | MODIFIER OR SHEAR | &simple &rightHandSide |
| % | QUANTIFICATION | breast@lump%2cm means lump at breast 2 cm in size. |
| ( ) | PROBABILITY | infection<plas-modium(0.7) means the probability of malaria is rated at 0.7. (−1) implies a certainty that it is not the diagnosis. |
| / | INCREASED | chest@pain/swallow (ches@pain/swal) reads as chest pain increases with swallowing. |
| \ | DECREASED | chest@pain\food (ches@pain\food) reads as chest pain decreased with food. |
| = | NORMAL | wcc = reads as white cell count is normal |
| * | ABNORMAL | fbe* |
| *l | ABNORMAL low | wcc*l means whiteCellCount abnormal low |
| *h | ABNORMAL High | wcc*h means whiteCellCount abnormal high |

Modifier Constructs for Docle Expressions

All modifiers start with the & character. Modifiers are required to qualify a code for a specific entity. An example is the therapeutic amoxycillin. This drug has as a secondary key amox. Modifiers are needed in constructing an electronic message to prescribe in a local or remote pharmacy. The modifiers for such an electronic prescribing system would comprise the following modifiers with its Docle notation:

| | |
|---|---|
| dose | &dose |
| presentation | &prese |
| quantity | &quan |
| repeat | &repe |
| EAN (industry number) | &ean |
| frequency | &freq |
| trade name | &tradn |
| route | &rout |
| not more | ¬m |
| special instructions | &spec |
| reason for prescribing | &rfp |

Hence an electronic prescription to the pharmacist, in the pre-emptive prescription method, will have the following string of characters in the message:

amoxycillin &tradn%amoxil &dose%1@8hi &prese%250mg@20caps &quan%20 &repe%0 &ean%123456789 &rfp%urti Graceful Deprecation—with Historical Shape Change Tolerance, and Avoidance of Reuse of Previously Deprecated Codes Problem definition of deprecated codes:

A. Codes are sometimes deprecated for a number of reasons. Among them is growth of scientific understanding leading to the splitting of the code into newer entities. Another reason being precision; if there is significant overlap of codes, then one code may have to go.
B. Having deprecated a code, and this code may be buried in someone's electronic medical record for years, there is need for a mechanism to prevent the use of the deprecated code by a new medical entity.
C. The need for the user to match the old deprecated code with the best-fit current code in an automated fashion to make use of the data.
D. The need to be able to reuse previously deprecated primary keys as new tertiary keys for other entities.
E. The need to preserve medical data as and when coded to preserve the 'context' of the coding process at that point in time.
F. The need to prevent a deprecated primary key to be used as a primary key again in the future after deprecation.

In this example we have a primary key, jakobCreutzfeldtDisease (jcd) that was in use for a while but is now (say 1$^{st}$ Jan 2000) deprecated.

The new code is
creutzfeldtJakobDisease with secondary key of cjd

Therefore the keys jakobCreutzfeldDisease and jcd are no longer found in either the primary or secondary keys tables.

The remedial actions taken by the maintainer of the Docle codes are:

A. make the deprecated primary key a tertiary key for the new primary code. Therefore jakobCreutzfeldDisease is now found in the tertiary keys table.
B. concatenate @ to the deprecated secondary key to create a new tertiary key for the new primary code. The resultant new tertiary key is @jcd.
C. concatenate @ to the deprecated primary key to create a new tertiary key for the new primary code. The resultant new tertiary key is @jakobCreutzfeldDisease.

The search algorithm for graceful deprecation, works with deprecated primary key or deprecated secondary key.

A. create new intermediate tertiary key by concatenating @ to the deprecated key.
B. key not found in keys (primary or secondary or tertiary) tables.
C. try accessing keys table.
D. if found, retrieve new code, exit.
E. if not found, generate new intermediate tertiary key by putting the intermediate tertiary key generated in step 2 by applying the docle algorithm.
F. try accessing keys table with this new intermediate tertiary key.
G. if found, retrieve new code, exit.
H. if not found, output message "sorry your code not recognised, but at least you can read what you coded".

In the hypothetical event, say it is now in the year 2020, that we want to use the deprecated old primary key jacobCreutzfeld disease again, we may do so, as a tertiary key for a newly discovered variant of dementia associated with heavy internet use (the primary key being dementia@internet). Hence when people coded for jacobCreutzfeldDisease in the year 2020 they get the primary/secondary code for dementia@internet. In that sense the key 'jacobCreutzfeldDisease' changes shape and can undergo an unlimited number of metamorphoses in a tertiary key role, but the Docle coding system tolerates its shape changes.

DESCRIPTION OF EXAMPLES AND FIGURES

Example 1

These two medical scripting files pertain to the same patient. In this extreme example there are two medical records held in two separate locations. In the first instance, on 6 Sep 1999, the patient is male and goes by the name of Joe Blow. He has a sexual preference problem which was diagnosed and treated the following day at another location where he had a sex change operation. The ADD operation on the two medical scripting files produce a new composite medical scripting file that captures and integrates all the events.

ADD operation on two medical scripting files pertaining to one patient.

|#administration |6 Sep 1999 marital%s |6 Sep 1999 kin%karen - sister |6 Sep 1999 fax%97649788 |6 Sep 1999 phh%97638411 |6 Sep 1999 email%jblow@connect.com |6 Sep 1999 phw%97638935 |6 Sep 1999 workplace%self |6 Sep 1999 zip%3179 |6 Sep 1999 state%vic |6 Sep 1999 suburb%scoresby |6 Sep 1999 country%australia |6 Sep 1999 preferredDoctor%oon |6 Sep 1999 dob%12 jun 1967 |6 Sep 1999 street%121 borg st |6 Sep 1999 account% |6 Sep 1999 pension% |6 Sep 1999 medicare% |6 Sep 1999 dolc% |6 Sep 1999 phm% |6 Sep 1999 markers% |6 Sep 1999 warning% |6 Sep 1999 firstname%joe |6 Sep 1999 surname%blow |6 Sep 1999 sex%m |6 Sep 1999 update%6 Sep 1999 |6 Sep 1999 comment% |6 Sep 1999 aka% |6 Sep 1999 name%blow joe || #command |6 Sep 1999 command@preventiveCare@hyperTension%%365%30% email |6 Sep 1999 command@preventiveCare@lung%%365%30%email |6 Sep 1999 command@preventiveCare@skin%%365%30%email |6 Sep 1999 command@preventiveCare@weight%%365%30%email |6 Sep 1999 command@preventiveCare@colon%%730%30%email l6 Sep 1999
command@exceptionReport%%36500%30%email l6 Sep 1999
command@preventiveCare@prostate%%730%30%email l6 Sep 1999
command@immunisation@hepatitisB%%1825%30%email l6 Sep 1999
command@immunisation@infl-uenza%%365%30%email l6 Sep 1999
command@immunisation@tetanus%%1825%30%email l6 Sep 1999
command@preventiveCare@alcohol%%1000%30%email l6 Sep 1999
command@preventiveCare@cholesterol%%730%30% email l6 Sep 1999
command@preventiveCare@diabetesMellitus%%365% 30%email ‖ #action ‖ #presentation ‖ #links ‖ #unity ‖ #management ‖ #book l ADD
l #administration l6 Sep 1999 fax%97649788 l6 Sep 1999 email%jblow@connect.com l6 Sep 1999 dob%12 jun 1967 l6 Sep 1999 marital%s l6 Sep 1999 firstname%joe l7 Sep 1999 firstname%jane l6 Sep 1999 phh%97638411 l6 Sep 1999 country%australia l6 Sep 1999 zip%3179 l6 Sep 1999 state%vic l6 Sep 1999 suburb%scoresby l7 Sep 1999 sex%f l6 Sep 1999 phw%97638935 l7 Sep 1999 surname%blow l7 Sep 1999 surname%blowina l6 Sep 1999 street%121 borg set l6 Sep 1999 pension% l6 Sep 1999 preferredDoctor% l6 Sep 1999 medicare% l6 Sep 1999 account% l6 Sep 1999 phm% l6 Sep 1999 workplace% l6 Sep 1999 warning% l7 Sep 1999 name%blowina jane l6 Sep 1999 comment% l6 Sep 1999 markers% l7 Sep 1999 update%7 Sep 1999 l6 Sep 1999 kin% l7 Sep 1999 aka%janee l7 Sep 1999 dolc% ‖ #command l6 Sep 1999
command@preventiveCare@lung%%365%30%email%email l6 Sep 1999
command@preventiveCare@skin%%365%30%email%email l6 Sep 1999
command@preventiveCare@weight%%365%30%email%email l6 Sep 1999
command@preventiveCare@hyperTension%%365%30%email%email l6 Sep 1999
command@preventiveCare@cervix%%730%30%email%email l6 Sep 1999
command@exceptionReport%%36500%30%email%email l6 Sep 1999
command@preventiveCare@osteoPorosis%%1095%30%email%email l6 Sep 1999
command@preventiveCare@breast%%730%30%email%email l6 Sep 1999
command@immunisation@hepatitisB%%1825%30%email%email l6 Sep 1999
command@immunisation@infl-uenza%%365%30%email%email l6 Sep 1999
command@immunisation@tetanus%%1825%30%email%email l6 Sep 1999
command@preventiveCare@diabetesMellitus%%365%30%email%email l6 Sep 1999
command@preventiveCare@cholesterol%%730%30%email%email l6 Sep 1999
command@preventiveCare@colon%%730%30%email%email l6 Sep 1999
command@preventiveCare@alcohol%%1000%30%email%email ‖ #action ‖ #presentation l7 Sep 1999 problem@sexualPreference ‖ #links ‖ #unity ‖ #management l7 sep 1999 surgery@sex@change ‖ #book l Example 2

The result of the ADD operation on the two disparate files on the same patient who has had the sex change operation. There has been a name and sex change as denoted in the administrative data. Note that the latest version of administrative data as determined by the time stamp which is up to the nearest one thousandth of a second, enables fine grain events to be discriminated and differentiated and allows data to be preserved. In this methodology, the access to a historical record of patient demographic and clinical data is assured. Time serial items such as addresses, phone numbers, onset of pill prescriptions, time of discontinuation and sundry clinical events are all documented in this longitudinal record.

Result of ADD Operation in Example 1
l#administration l6 Sep 1999 marital%s l6 Sep 1999 kin%karen - sister l6 Sep 1999 fax%97649788 l6 Sep 1999 phh%97638411 l6 Sep 1999 email%jblow@connect.com l6 Sep 1999 phw%97638935 l6 Sep 1999 workplace%self l6 Sep 1999 zip%3179 l6 Sep 1999 state%vic l6 Sep 1999 suburb%scoresby l7 Sep 1999 sex%f l6 Sep 1999 country%australia l6 Sep 1999 preferredDoctor%oon l6 Sep 1999 dob%12 jun 1967 l6 Sep 1999 street%121 borg st l6 Sep 1999 account% l6 Sep 1999 pension% l6 Sep 1999 medicare% l6 Sep 1999 dolc% l6 Sep 1999 phm% l6 Sep 1999 markers% l6 Sep 1999 warning% l7 Sep 1999 firstname%jane l6 Sep 1999 firstname%joe l7 Sep 1999 surname%blowina l6 Sep 1999 surname%blow l7 Sep 1999 sex%f l6 Sep 1999 sex%m l6 Sep 1999 update%7 Sep 1999 l6 Sep 1999 comment% l7 Sep 1999 aka%janee l7 Sep 1999 name%blowina jane l6 Sep 1999 name%blow joe ‖ #command l6 Sep 1999
command@preventiveCare@hyperTension%%365%30% email l6 Sep 1999
command@preventiveCare@lung%%365%30%email l6 Sep 1999
command@preventiveCare@skin%%365%30%email l6 Sep 1999
command@preventiveCare@weight%%365%30%email l6 Sep 1999
command@preventiveCare@colon%%730%30%email l6 Sep 1999
command@exceptionReport%%36500%30%email l6 Sep 1999
command@preventiveCare@prostate%%730%30%email l6 Sep 1999
command@immunisation@hepatitisB%%1825%30%email l6 Sep 1999
command@immunisation@infl-uenza%%365%30%email l6 Sep 1999
command@immunisation@tetanus%%1825%30%email l6 Sep 1999
command@preventiveCare@alcohol%%1000%30%email l6 Sep 1999
command@preventiveCare@cholesterol%%730%30% email l6 Sep 1999
command@preventiveCare@diabetesMellitus%%365% 30%email ‖ #action ‖ #presentation l7 Sep 1999 problem@sexualPreference ‖ #links ‖ #unity ‖ #management l7 sep 1999 surgery@sex@change ‖ #book l

Example 3

A full blown example of a patient file coded in medical scripting language, comprising a single graphic element showing a laceration of the face. The OrderedCollection of points (series of numbers) represent the graphic in FIG. 3.

Example of a medical scripting language file with graphics embedded.

|#administration |6 Aug 1999 suburb%wheelers hill |6 Aug 1999 zip%3150 |6 Aug 1999 marital%s |6 Aug 1999 phw% |6 Aug 1999 kin%kuang juliet david |6 Aug 1999 pension% |6 Aug 1999 account% |6 Aug 1999 state%vic |6 Aug 1999 phh%5620242 |6 Aug 1999 medicare%3068 17540 4 |6 Aug 1999 phm% |6 Aug 1999 workplace% |6 Aug 1999 preferredDoctor%yko |6 Aug 1999 comment% |6 Aug 1999 warning% |6 Aug 1999 sex%f |6 Aug 1999 surname%oon |6 Aug 1999 name%oon nicole |6 Aug 1999 street%21 erskine drive |6 Aug 1999 firstname%nicole |6 Aug 1999 dob%27 sep 1990 |6 Aug 1999 aka% |6 Aug 1999 country% |6 Aug 1999 dolc%20 mar 1992 |6 Aug 1999 markers% |5 Sep 1999 email%nicole@compuserve.com |5 Sep 1999 update%5 Sep 1999 |5 Sep 1999 fax%0397649788 ||
command |6 Aug 1999 command@preventiveCare@skin%%365%30%email |6 Aug 1999
command@immunisation@hepatitisB%%1825%30%email |6 Aug 1999
command@preventiveCare@diabetesMellitus%%365%30%email |6 Aug 1999
command@exceptionReport%%36500%30%email |6 Aug 1999
command@preventiveCare@hyperTension%%365%30%email |6 Aug 1999
command@preventiveCare@weight%%365%30%email |6 Aug 1999
command@preventiveCare@colon%%730%30%email |6 Aug 1999
command@preventiveCare@lung%%365%30%email ||
action || #presentation |8 Feb 1999 vision@double,harry wenas, diplopia
?manifestation of phoria, eye alignm
quite good |27 Jun 1999 vision@blur review by wenas, vision 6/5
in each eye, good control eye movem |5 Sep 1999 cough |5 Sep 1999 abdomen@pain || #links |5 Sep 1999 fullBloodExamination=|| #unity |5 Sep 1999 mesentericAdenitis || #management |5 Sep 1999 amoxycillin || #book | #images@polyline |5 Sep 1999 laceration %OrderedCollection (OrderedCollection (218@66 217@66 216@66 214@66 213@66 212@66 210@66 208@66 205@66 202@66 199@66 197@67 196@68 194@69 194@71 192@72 190@74 188@75 186@77 183@79 182@82 180@84 178@87 176@90 174@93 172@95 171@98 170@99 169@100 169@101 168@101 168@103 168@104 168@107 168@111 168@113 168@114 168@115) OrderedCollection (218@73 219@72 220@72 222@71 224@70 227@69 230@69 233@69 236@69 240@69 244@69 248@70 252@71 256@72 259@73 263@75 267@78 271@81 274@83 276@86 278@88 279@90 281@93 282@96 283@99 285@101 286@105 287@107 287@111 288@113 289@116 290@120 291@124 291@129 293@133 295@135 295@136 296@137 297@138 297@139 299@140 301@141 303@142 304@143 305@144 306@144 307@145 307@146 307@145) OrderedCollection (232@61 233@59 235@57 238@56 241@55 246@55 251@54 257@54 271@55 285@57 290@59 293@61 296@63 299@66 302@69 306@72 308@75 311@78 313@81 314@84 315@88 316@92 316@97 316@101 316@106 316@111 316@116 316@120 316@123 317@126 317@130 318@133 318@136 318@137 319@137 319@135 319@133) OrderedCollection (241@52 241@50 243@48 245@46 247@45 250@43 253@43 259@42 273@42 287@42 293@43 298@43 301@45 304@47 306@49 308@51 310@55 313@59 316@64 319@68 321@73 322@78 323@83 324@89 324@103 324@119 324@133 324@139 324@142 324@144 324@147 324@146 324@144) OrderedCollection (223@47 222@45 221@45 220@44 219@44 217@43 215@43 212@43 208@43 203@44 198@46 194@47 191@50 188@52 186@54 182@58 180@61 178@64 176@68 174@71 174@76 173@81 172@86 171@92 170@98 170@103 170@107 170@111 170@115 172@112) OrderedCollection (218@59 214@59 211@59 207@59 204@60 201@61 197@63 192@65 189@69 186@72 182@76 178@80 176@85 174@90 173@96 172@102 172@107 172@111 172@113 172@112 173@110 174@108) OrderedCollection (224@55 224@54 223@52 221@50 219@47 216@44 213@43 210@42 207@40 204@40 200@40 195@40 192@40 187@40 181@42 175@45 169@48 164@51 160@55 158@59 156@63 155@66 154@69 154@70 154@71 156@71 158@71 161@71) OrderedCollection (232@38 231@37 228@35 226@33 223@32 220@31 217@30 213@30 210@30 206@30 201@30 196@31 192@33 187@34 182@37 180@39 177@42 174@45 172@49 169@55 167@61 166@67 164@73 163@78 162@83 161@87 160@92 159@97 159@99 159@101 159@102 160@102 163@100 166@98) OrderedCollection (189@31 183@31 178@31 173@32 168@34 164@37 162@40 160@44 159@48 157@54 156@59 154@65 153@70 152@76 151@81 151@86 151@91 151@95 151@99 151@101 151@103 151@104 151@105 152@106 154@109 156@112 159@115 160@117 161@118 162@118 163@115) OrderedCollection (243@35 241@37 240@39 239@42 239@44 239@45 240@44 242@41 244@39 247@36 250@34 254@33 258@32 272@32 288@33 302@36 316@40 321@44 325@49 329@55 331@61 333@77 335@93 337@107 337@112 337@115 337@116 338@116 337@115 335@111) OrderedCollection (251@42 251@41 251@39 251@37 252@33 254@29 257@26 261@23 267@22 283@21 289@21 292@22 293@23 294@25 294@29 294@33 295@37 296@40) OrderedCollection (242@21 243@19 246@18 250@18 255@18 259@18 264@20 267@22 268@24 268@26 269@29 270@32 271@34) OrderedCollection (233@23 228@23 225@23 221@25 218@27 217@28 217@29) OrderedCollection (163@120 163@121 164@121 165@121 166@121 167@121 168@121 168@120 168@122 168@124 168@127 168@131 168@135 168@141 168@147 168@153 168@158 168@164 168@170 168@175 168@179 168@184 168@189 168@194 168@199 168@203 168@206 168@209 168@212 168@214 168@216 169@218 169@221 170@224 170@227 171@229 172@232 173@235 174@237 175@239 176@242 177@243 178@246 179@247 180@250 181@251 182@253 182@254 183@254 183@255 183@256 184@258 185@259 186@260 187@260 187@261 188@262 189@262 190@263 191@263 191@264 192@264 193@264 194@265 195@266 196@266 197@266 198@267 199@267 200@267 201@268 204@269 207@270 209@270 211@271

212@271 213@272 214@272 216@272 218@273
221@274 223@274 224@274 225@274 226@274
228@274 229@274 231@274 234@273 236@273
239@272 241@271 245@270 250@269 254@268
258@267 261@265 264@264 266@262 269@261
271@259 273@256 276@254 280@252 282@248
285@244 288@241 290@238 292@234 294@230
296@226 298@222 301@218 304@214 306@211
308@208 310@204 312@200 313@196 315@192
317@187 319@183 320@180 322@176 324@172
325@168 326@166 327@164 328@161 329@160)
OrderedCollection (318@140 318@139 318@138
319@137 320@135 322@134 323@133 324@133
325@133 326@133 327@133 328@133 328@134
328@135 328@137 328@140 328@143 328@145
327@148 326@152 325@156 325@159 324@163
323@165 323@167 322@169 321@171 321@172
320@175 318@177 317@179 316@182 314@185
313@188 311@191 310@193 309@194 309@195
308@196 307@196 305@193 301@189 298@184
296@181 295@178 295@177 295@176 296@176
297@176) OrderedCollection (311@161 312@161
312@160 313@158 314@156 316@153 317@152
319@150 320@149 320@148 321@148 321@150
321@152 321@155 320@158 319@162 317@166
315@169 314@171 312@173 312@175 311@176
310@176 310@175 310@174) OrderedCollection
(241@149 242@149 243@148 244@148 245@146
247@145 249@145 251@144 252@144 253@144
254@144 255@144 256@144 257@145 259@146
261@147 263@148 265@148 268@149 269@149
270@149 271@149 272@149 273@149 275@149
276@149 274@149)

OrderedCollection (206@149 207@149 207@148
206@148 205@146 203@146 202@145 201@145
201@144 200@144 199@144 198@144 197@144
195@144 194@144 192@144 191@144 190@144
189@144 188@144 187@144 186@144 185@144
183@145 181@146 181@147 180@147 179@147
178@148 178@149) OrderedCollection (224@144
224@146 224@148 223@150 223@152 223@154
222@157 221@159 221@161 220@163 219@166
218@168 217@171 216@172 216@173 215@174
215@175 214@176 214@177 213@179 213@180
212@182 211@183 211@185 210@186 210@188
210@189 209@190 209@191 208@192 208@193
208@194 210@194 211@195 212@195 213@195
214@195 215@195 216@195 218@195 220@195
221@195 222@195 222@194 223@194 224@194
225@194 226@194 227@194 228@195 229@195
230@195 230@196 231@196 232@196 233@196
234@196 235@195 235@194 236@193 236@192
236@191 236@193) OrderedCollection (203@223
203@222 204@222 205@221 206@221 207@221
208@220 209@220 210@220 211@220 212@220
213@220 214@220 215@220 216@220 217@220
218@220 219@220 220@220 221@220 222@220
222@219 223@219 224@219 225@219 226@220
227@221 228@222 230@222 230@223 231@224
232@224 233@225 234@225 235@225 236@225
237@225 238@225 240@225 241@225 243@225
246@225 247@225 248@224 248@223 249@223)
OrderedCollection (200@224 201@224 203@224
205@225 208@225 211@226 213@226 215@227
217@227 218@227 219@227 220@228 222@228
223@228 225@228 226@228 227@228 228@228
230@228 232@228 233@227 234@227 235@227
236@227 236@226 237@226 236@226 235@226)
OrderedCollection (207@222 208@222 209@222
211@222 214@222 216@222 218@222 220@222
222@222 224@222 225@222 226@222 227@222
228@223 229@223 230@224 231@224 232@225
232@226 233@226)

OrderedCollection (250@150 250@151 250@152
251@153 252@153 252@154 253@154 254@154
255@154 256@154 257@154 258@153 258@152
258@151 258@150 257@149 255@149 253@149
252@148 251@148 250@148) OrderedCollection
(195@150 194@150 193@150 192@150 191@150
191@151 191@152 191@153 191@154 191@155
191@156 191@157 192@158 193@158 194@158
195@158 196@158 196@157 196@156 196@155
196@154 195@153 192@152 190@151 189@151)
OrderedCollection (313@191 312@192 312@193
312@195 312@197 312@199 312@201 311@203
311@206 311@208 311@211 311@213 310@216
310@219 310@221 310@223 310@226 310@229
310@233 310@236 311@239 312@242 312@244
313@246 313@248 313@249 314@251 315@253
316@255 317@257 318@259 319@259 319@260
320@261 321@262 321@263 322@264 323@264
323@265 322@265) OrderedCollection (192@260
192@261 192@262 192@263 192@264 192@265
192@266 192@267 192@268 192@269 192@270
192@271 192@272 192@273 191@274 191@275
190@276 190@277 189@277 188@278 188@279
187@279 187@280 186@280 185@281 184@281
183@282 182@283 181@283 180@283 179@283
180@282) OrderedCollection (233@101 234@101
235@101 236@101 237@102 238@102 239@103
240@104 243@104 245@106 246@106 247@107
248@108 249@109 250@110 252@111 254@112
255@113 256@114 257@114 257@115 258@115
259@116 260@116 260@117 261@118 262@118
263@119 263@120 264@120) OrderedCollection
(241@108 241@107 241@106 241@105 241@104
241@103 242@102 242@101 242@102 242@103)
OrderedCollection (246@111 246@110 246@109
247@109 247@108 247@107 248@107 248@106
248@105 249@105) OrderedCollection (253@117
254@116 254@115 255@115 255@114 255@113
256@113 256@112 256@111 257@111 257@110
258@110)

OrderedCollection (260@120 261@120 262@120
262@119 263@118 263@117 264@117))|

In FIG. 1 there is shown an algorithm for the ADD operation on two medical scripting language files. The files are concatenated and parsed event for event. The context for the parser is set by the Ordered Collection Categories keywords such as #administrative #command #action #presentation #links #unity #book #management #images.

Figure 2:
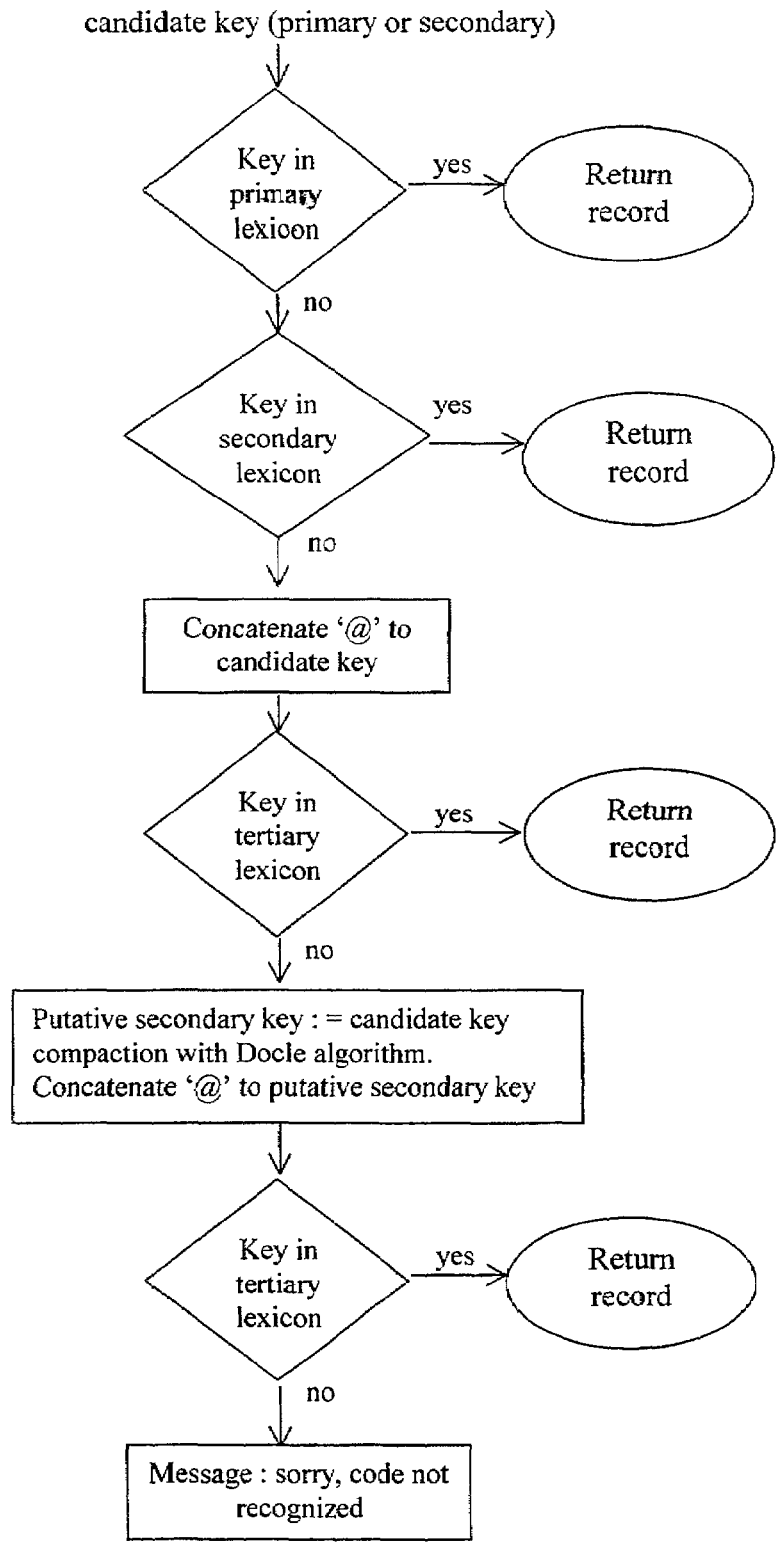

In FIG. 2 there is shown a search algorithm for deprecated primary and secondary Docle keywords allows for keyword change tolerance in the patient medical scripting language file. This "shape change tolerance" for coping with change in the meaning of codes in medical files is a useful feature when the medical record is used as a tool in medical research.

Figure 3:

FIG. 3 shows a printout of a graphic element embedded in the medical scripting language file of Example 3 above.

Figure 4:
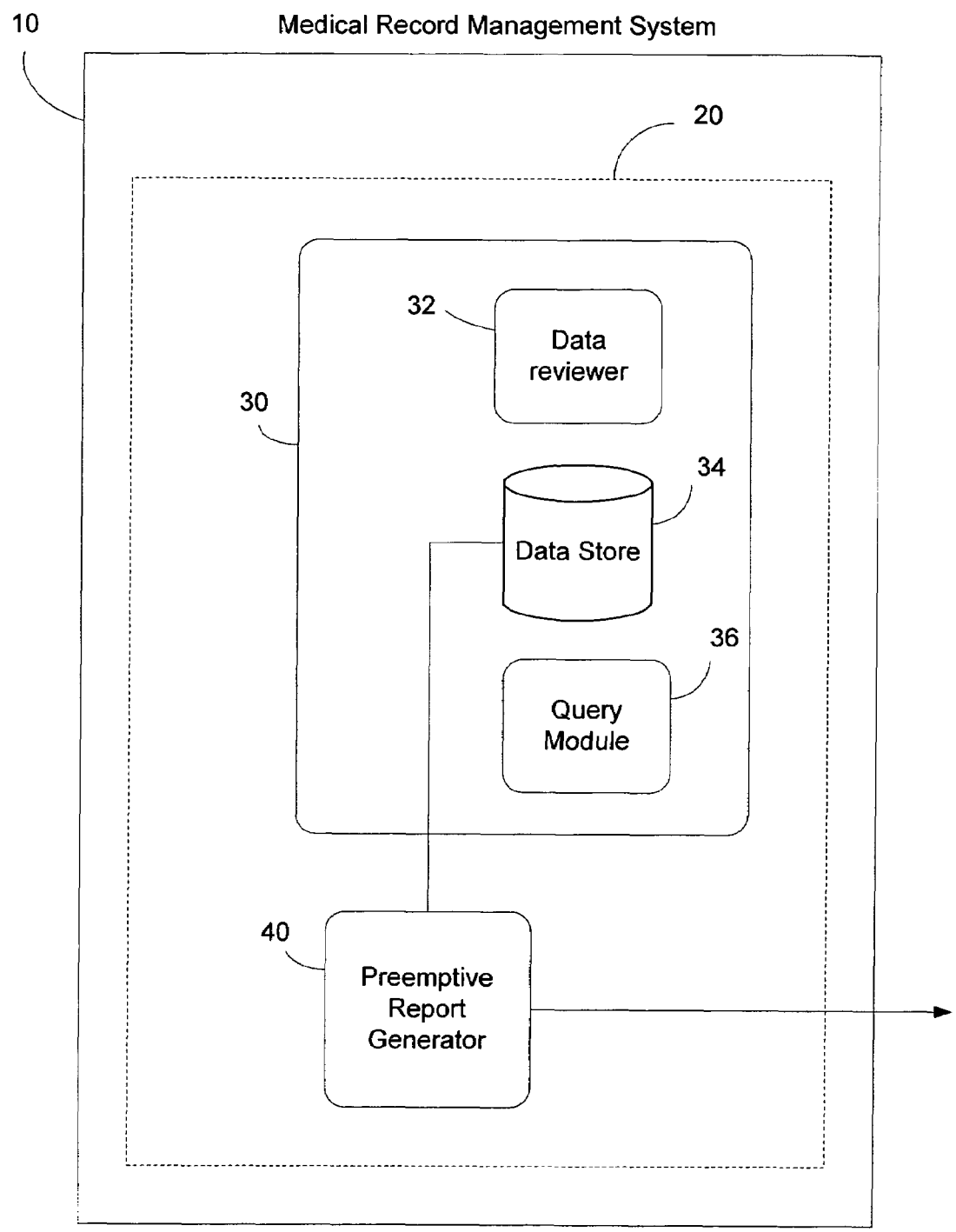

FIG. 4 shows in a schematic form the medical record management system 10 of the invention. The computerized medical record management system 10 runs on a computer or computer network 20 and comprises an administrator system 30, a data reviewer 32, a data store 34, a query module 36, and a preemptive report generator 40.

The word 'comprising' or forms of the word 'comprising' as used in this description and in the claims do not limit the invention claimed to exclude any variants or additions.

The invention claimed is:

1. A computerized medical record management system comprising means for generating, storing, retrieving and updating patient medical records represented in a medical scripting language having predetermined syntactical and semantic constructs, comprising:
  (a) an administrator system having:
    (i) a data receiver to selectively receive one or more medical records and pertaining to a patient, each record represented in a medical scripting language having predetermined syntactical and semantic constructs, being defined in Extended Backus Naur Format and being suitable both for machine interpretation and for human readability and human veracity checking, each record represented in said medical scripting language including script instructions that contain embedded commands;
    (ii) a data store in operative interconnection with the data receiver and configured to store each patient medical record on the basis of patient data categorised into event categories of patient presentation data, patient test results data, patient diagnosis data, and medication data;
    (iii) a query module in operative interconnection with the data store and configured to receive a query from a predefined source which has been assigned selective access to the patient medical records stored therein, and to transmit relevant record data to that source to allow retrieval and updating of stored records; and
  (b) a pre-emptive report generator in operative interconnection with the data store configured to interrogate the medical records represented in the medical scripting language in accordance with prescribed instructions to initiate report generation and execution of said embedded commands in accordance with preselected criteria.

2. The system of claim 1, further comprising at least one of a computer and a computer network on which said data receiver, data store, query module and report generator are installed.

3. The system of claim 1, wherein said medical scripting language having predetermined syntactical and semantic constructs utilizes character strings in one of ASCII format and Unicode character sets.

4. The system of claim 1, wherein said medical records further comprise event constructs, each event construct including the components of a date/time header field, a linnean medical word field, a comment field, a signature field, an accession detail field, and an event status field.

5. The system of claim 1, wherein said pre-emptive report generator further comprises means to carry out reminder and recall actions with respect to said embedded commands within the patient records.

6. A method for managing computerised medical records, involving the generation, storing, retrieval and updating of patient medical records represented in a medical scripting language having predetermined syntactical and semantic constructs, the method comprising the steps of:
  (a) using a data receiver to selectively receive one or more medical records pertaining to a patient, each record represented in a medical scripting language having predetermined syntactical and semantic constructs, being defined in Extended Backus Naur Format and being suitable both for machine interpretation and for human readability and human veracity checking, each record represented in said medical scripting language including script instructions that contain embedded commands;
  (b) using a data store in operative interconnection with the data receiver to store each patient medical record on the basis of patient data categorised into event categories of patient presentation data, patient test results data, patient diagnosis data, and medication data;
  (c) using a query module in operative interconnection with the data store to submit a query to the data store from a predefined source which has been assigned selective access to the patient medical records stored therein;
  (d) transmitting relevant record data to said source to allow retrieval and updating of stored records; and
  (e) using a pre-emptive report generator in operative interconnection with the data store to interrogate the medical records in accordance with prescribed instructions in order to initiate report generation and execution of said embedded commands in accordance with preselected criteria.

7. The method of claim 6 carried out on a computer or computer network on which said data receiver, data store, query module and report generator are installed.

8. The method of claim 6, wherein said medical scripting language having predetermined syntactical and semantic constructs utilizes at least one of character strings in ASCII format and Unicode character sets.

9. The method of claim 6, said medical records comprising event constructs, each event construct including the components of a date/time header field, a linnean medical word field, a comment field, a signature field, an accession detail field, and an event status field.

10. The method of claim 6, further comprising the step of using said pre-emptive report generator to carry out reminder and recall actions with respect to said embedded commands within the patient records.

* * * * *